United States Patent
Akiyoshi et al.

[11] Patent Number: 5,844,149
[45] Date of Patent: Dec. 1, 1998

[54] METHOD FOR ANALYZING SOLID SPECIMEN AND APPARATUS THEREFOR

[75] Inventors: Takanori Akiyoshi; Akiko Sakashita; Yohichi Ishibashi; Tadashi Mochizuki; Shigeomi Sato; Toshiya Maekawa, all of Tokyo, Japan

[73] Assignee: NKK Corporation, tokyo, Japan

[21] Appl. No.: 764,141

[22] Filed: Dec. 12, 1996

[30] Foreign Application Priority Data

Sep. 19, 1996 [JP] Japan .................................... 8-247357

[51] Int. Cl.⁶ ...................................................... G01N 1/04
[52] U.S. Cl. ...................................................... 73/864.81
[58] Field of Search .......................... 73/864.81, 863.11; 356/36; 250/423 P, 425

[56] References Cited

U.S. PATENT DOCUMENTS

| | | | |
|---|---|---|---|
| 4,243,887 | 1/1981 | Hillenkamp et al. | 250/423 |
| 5,304,357 | 4/1994 | Sato et al. | 118/50.1 |
| 5,351,251 | 9/1994 | Hodgson | 372/4 |
| 5,452,070 | 9/1995 | Mochizuki et al. | 356/36 |

FOREIGN PATENT DOCUMENTS 3 203 912 A1   8/1983   Germany .
4 028 102 A1   3/1992   Germany .

OTHER PUBLICATIONS

*English language Abstract of No. 7-72047, Japan, Mar., 1995.

*Primary Examiner*—Robert Raevis
*Attorney, Agent, or Firm*—Frishauf, Holtz, Goodman, Langer & Chick

[57] ABSTRACT

A method for analyzing a solid specimen comprises the steps of: preparing a pulsed laser beam having a frequency of at least 100 Hz and a half width of 1 $\mu$sec or less; determining a laser irradiation region; irradiating the pulsed laser beam in an inert gas stream and vaporizing a part of the solid specimen to generate fine particles; transferring said fine particles to a detector; and performing elemental analysis in the detector. An apparatus comprises: laser oscillating device including a semiconductor laser; converging device for converging a laser beam; irradiating device for irradiating the converged laser beam to generate fine particles; an analyzer for performing elemental analysis; and transfer device for transferring the fine particles to said analyzer.

9 Claims, 21 Drawing Sheets

| | PRESENT INVENTION | | CONVENTIONAL METHOD |
|---|---|---|---|
| ① :COLLECTION | 12 SEC | | 12 SEC |
| ② :TRANSFER | 22 SEC | | 22 SEC |
| ③ :CUTTING | 15 SEC | | 20 SEC |
| ④ :COOLING | OMISSION | AUTOMATIC PROCEDURE → | 25 SEC |
| ⑤ :GRINDING | OMISSION | | 35 SEC |
| ⑥ :ANALYSIS | 30 SEC | | 56 SEC ← AUTOMATIC PROCEDURE |
| TOTAL | 79 SEC | | 170 SEC |

FIG.19

METHOD FOR ANALYZING SOLID SPECIMEN AND APPARATUS THEREFOR

BACKGROUND OF THE INVENTION

1. Field of the Invention

The present invention relates to a method and an apparatus for analyzing a solid specimen. In particular, the present invention relates to a method and an apparatus in which a laser beam is irradiated onto the surface of a solid specimen to collect fine particles and the fine particles are transferred to an analyzer for elemental analysis.

2. Description of the Related Arts

In conventional laser vaporization analysis, a converged laser beam pulse is irradiated onto the surface of a solid mother specimen, e.g. metal or ceramic, in an inert gas stream to vaporize a part of the mother specimen, a fine particle specimen obtained by cooling the vaporized specimen is transferred to an analyzer in the inert gas stream to serve for elemental analysis, the elements in the mother specimen being determined from the analytical results of the fine particle specimen. A typical example of the laser vaporization analytical technique is disclosed, for example, in Japanese Unexamined Patent Publication No. 7-72047, in which, concerning laser irradiation conditions, the range of the selective vaporization ratio (the ratio of the analytical concentration of an element in the fine particles to the concentration of the element in the mother specimen) is determined depending on the amount of the fine particles yielded, and the laser beam pulse is irradiated at an energy density of 100 kW/mm$^2$ to 500 MW/mm$^2$, a frequency of 100 Hz or more, and a pulse half width of 50 to 400 nsec.

However, such laser irradiation conditions are for analysis with a relative standard deviation within 5%. Since practical spark emission spectrometry has a relative standard deviation of less than 2%, the laser vaporization analysis requires an accuracy the same as that of spark emission spectrometry.

SUMMARY OF THE INVENTION

It is an object of the present invention to provide a method for analyzing a solid specimen and an apparatus therefor in which the analytical accuracy is improved and the size and weight of the apparatus are reduced.

In order to achieve the object, the present invention provides a method for analyzing a solid specimen comprising the steps of:

(a) preparing a pulsed laser beam;

(b) determining a laser irradiation region;

(c) irradiating the pulsed laser beam to generate fine particles;

(d) repeating the step (c) to further generate fine particles;

(e) transferring the fine particles to a detector; and (f) performing elemental analysis in the detector.

In the step (a), the pulsed laser beam has a frequency of at least 100 Hz and a half width of 1 $\mu$sec. or less.

In the step (b), the laser irradiation region is determined so that the energy density satisfies the following equation:

$$Q > t^{1/2} \times \alpha / r$$

wherein Q represents energy density (J/cm$^2$), t represents pulse half width, $\alpha$ represents a parameter inherent to the analytical specimen, and r represents absorption coefficient of a laser beam.

In the step (c), the fine particles are formed by irradiating pulsed laser beam on the irradiation region on the surface of the solid specimen in an inert gas stream and vaporizing a part of the specimen.

In the step (d), fine particles are further generated by repeating the irradiation on the same surface that the pulsed laser beam is irradiated in the step (c). In the step (c) and (d), the laser are irradiated from a laser oscillating means including a semiconductor laser.

Further, the present invention provides an apparatus for analyzing a solid specimen comprising:

laser oscillating means including a semiconductor laser;

converging means for converging a laser beam oscillated from the laser oscillating means;

fine particle forming means for irradiating the converged laser beam onto a surface of the solid specimen to vaporize a part of the specimen and to generate fine particles;

an analyzer for performing elemental analysis of the fine particle specimen; and transfer means for transferring the fine particles to the analyzer.

The laser oscillating means can comprise the semiconductor laser, a laser rod, and an optical fiber cable. The semiconductor laser generates a laser beam, the laser rod receives the laser beam from the semiconductor laser, and the optical fiber cable connects the semiconductor laser and the laser rod.

The laser oscillating means can comprise the semiconductor laser, the laser rod, and resonators provided at the both ends of the laser rod. The laser oscillating means can comprise a semiconductor laser as a pumping light source, a solid laser medium for continuously oscillating a Q switch laser beam, and a Q switch element.

The converging means can comprise a condenser lens for converging the laser beam from the laser oscillating means on the surface of the specimen, and a focal point swinging means for swinging the focal point of the laser beam on the surface of the specimen for a predetermined amplitude.

The transfer means can comprise a transfer cell for transferring the fine particle specimen to the analyzer by means of close contact with the specimen The focal point swinging means can comprise a lens swinging means for swinging the condenser lens in the vertical and horizontal directions perpendicular to the radiated laser beam for a predetermined amplitude.

Alternatively, the focal point swinging means can comprise two sets of scanning mirrors of which the axes are perpendicular to each other, ultrasonic motors for reciprocating the scanning mirrors at predetermined angles, and a condenser lens; wherein the axis of the laser beam is vertically and horizontally swung by means of reciprocal rotation of the scanning mirrors.

Alternatively, the focal point swinging means can comprise an acoustooptic deflector for deflecting the axis of the laser beam so as to draw a plane.

Furthermore, the present invention provides a method for analyzing a solid specimen comprising:

irradiating a pulsed laser beam on the solid specimen to generate fine particles; and determining components of the fine particles:

characterized by:

continuously moving a position to be analyzed at a predetermined speed;

measuring momentary values in which the components of the fine particles are measured at a minute time interval; and determining a quantity of an objective component contained in the homogeneously dissolved section and a quantity of the component contained in the inhomogeneously dissolved section, by means of analysis of the momentary values.

BRIEF DESCRIPTION OF THE DRAWINGS

FIG. 19 is a table in which the analysis time in a conventional emission spectrometry technique is compared with that in a laser ICP analysis method;

DETAILED DESCRIPTION OF THE PREFERRED EMBODIMENTS

Figure 1:
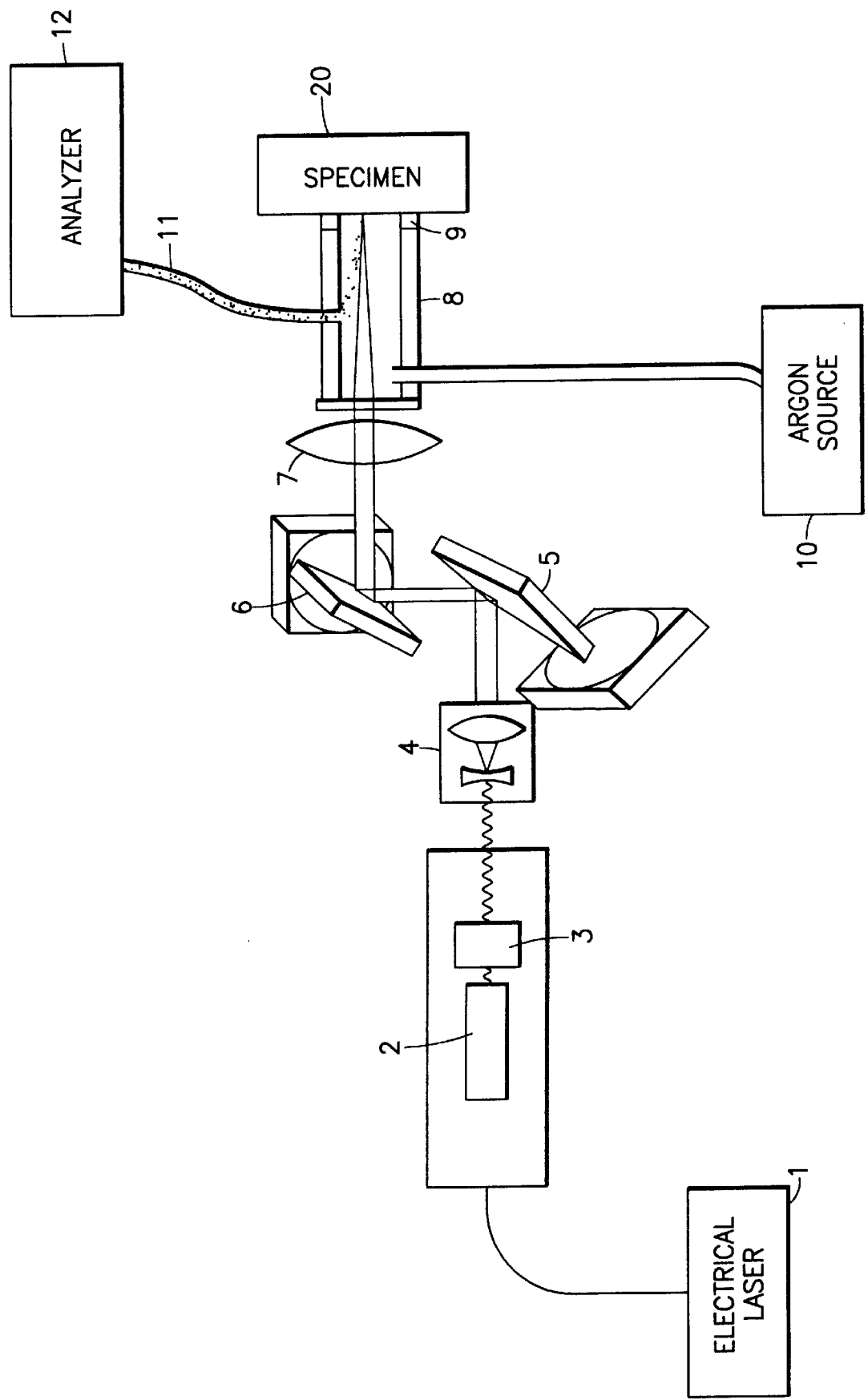
FIG. 1 is a block diagram illustrating an apparatus configuration in which a laser vaporization analytical method in accordance with an embodiment of the present invention is applied.

In accordance with the present invention, a pulsed laser beam having a frequency of 100 Hz or more and a half-width of 1 $\mu$sec. or less are irradiated onto an irradiation surface of a specimen, in which the irradiation energy density satisfies a threshold value determined by thermal and optical absorbance characteristics of the analytical specimen, by two-dimensional scanning over all the irradiation surface, and the same irradiation surface is etched to form fine particles by means of repeated irradiation cycles. For example, the diameter of the irradiated spot on the specimen is set to be 10 $\mu$m or more, laser irradiation conditions and optical system are set so that the average energy density satisfies the following equation (1), the laser beam is two-dimensionally scanned over the entire irradiation surface, and the same irradiation surface is repeatedly irradiated to form fine particles:

$$Q > t^{1/2} \times \alpha/r \ (\text{J/cm}^2) \tag{1}$$

wherein t represents the pulse half width of the laser, $\alpha$ represents the parameter inherent in the analytical specimen, and r represents the absorption coefficient of a laser beam.

The absorption coefficient r is determined based on the following equation: r=Qa/Qt. In the equation, Qa is a absorption heat of specimen and Qt is a total irradiation heat. The laser beam having the irradiation power P (W) is irradiated to the specimen for t seconds and the absorption heat Qa of specimen is measured in a condition that the the specimen is not vaporized without applying the Q-switch. The total irradiation heat Qt is calculated by the following equation; Qt=W×t/4.2 (cal.).

The parameter $\alpha$ is determined as follows. In pure substance such as pure metal, the laser beams having the differen energy density are irradiated on the specimen having the predetermined absorption coefficient r. The threshold value of the energy density is determined from the physical characteristic of the sample spot. At the threshold value, the specimen is vaporized and the sample spot becomes hole shape. The parameter $\alpha$ is determined from the threshold value of the energy density and the absorption coefficient r. In the specimen in which a plurality of elements are contained, each of $\alpha$ parameters is obtained as pure element and the highest $\alpha$ parameter among the elements can be adopted. As another method, the $\alpha$ parameter may be obtained from the relationship between a composition ratio and the energy density. The composition ratio is the ratio of the content of the element having the highest $\alpha$ parameter to the content of the element which is contained most. The $\alpha$ parameter can be obtained from the stable energy density having high composition ratio and the absorption coefficient r.

For highly reliable laser vaporization analysis, the formed fine particles must satisfy the following characteristics:

(1) The composition of the fine particles is very similar to that of the mother specimen; that is, the selective vaporizaion ratio is almost equal to 1;

(2) The size of the fine particles has a mono-dispersive distribution for ease of vaporization with decomposition in the analyzer.

A selective vaporizaion ratio far from 1 means that the ratio of selective vaporization of the specimen increases during laser irradiation with a large variation in ratio, and the quantity of the specimen must increase to compensate for the variation. A stable selective vaporizaion ratio near 1 forms fine particles having almost identical composition with little variation and results in highly accurate analysis.

The following are laser irradiation conditions essential for the preparation of such fine particles:

(a) The position on which the laser beam is irradiated is promptly heated to a high temperature so as to vaporize all the components in the specimen. After the laser irradiation, the position is promptly cooled so that selective vaporization due to differing vapor pressures and due to heat conduction can be suppressed;

(b) Melting is minimized during laser irradiation, and formation of fine particles due to scattering of the melt is minimal.

The effects of the laser beam on a material include a main effect i.e., heat formation due to laser beam absorption when the power of the radiating laser beam is not very high, and a break-down effect in which the material is directly ionized in the electric field generated by the significantly high powered electromagnetic wave of laser beam. The external energy for vaporizing the specimen depends on the thermal conductivity, specific heat, density, melting temperature, heat of fusion, vaporizing temperature and heat of vaporization. In the case of a laser beam energy source, the external energy also depends on the laser absorption efficiency of the specimen. The laser absorption efficiency depends on the absorption efficiency inherent in the specimen and the surface characteristics of the specimen, e.g. roughness and contamination. When the energy density of the laser beam radiated onto a predetermined region is higher than the threshold value, all the components in the specimen are promptly vaporized, as set forth above (a). The threshold value is inherent in the specimen and varies with thermal conductivity, heat of vaporization and the like, as set forth above.

For example, a temperature at which pure metals having high boiling points, e.g. Mo and W can be vaporized is set as a temperature condition for vaporizing all the components in a metallic specimen. During irradiation at a lower temperature, metals having high boiling points accumulate in the upper surface layer to form an almost pure metal state which significantly inhibits laser evaporation of the specimen. The vaporization condition of W as a pure metal having a high boiling point was investigated. The pulse energy was 0.04 mJ and the diameter of the focused beam was 60 $\mu m\phi$, for a radiated single mode laser beam having a half-width of 20 nsec. A significant difference between the pure material and a mixture such as an alloy is the absorbance of the laser light. For example, pure copper has an absorbance of 0.02 for light having a wavelength of 1 $\mu m$, whereas copper included in steel has an absorbance at least ten fold higher. Since ceramic specimens can vaporize more quickly with the same irradiation energy because of their lower thermal conductivity, the temperature condition for pure metals having high boiling points can be satisfactorily applied to the ceramic specimens. However, since very severe vaporization conditions are required for materials having high laser transmittance such as quartz glass, the irradiation conditions must be determined in consideration to laser absorption efficiency.

Since a practical laser beam has a planer energy distribution, it is difficult for the entire surface irradiated with the laser beam to satisfy the conditions. Thus, selective vaporization is performed with single pulse irradiation. When the laser beam uniformly scans and radiates over a wide area in which individual spot diameters are negligible, and when the laser beam is repeatedly radiated onto this area so that the effects of individual irradiated pulses are negligible in the depth direction, selective vaporization does not substantially occur.

If selective vaporization does occur to some extent during single pulse irradiation, the residual surface composition of the mother specimen is the reverse of the composition of the formed fine particles, i.e., the more easily vaporized components are diluted and the less easily vaporized components are concentrated. When such a residual surface is irradiated with single pulse irradiation, fine particles having a composition similar to the composition of the mother sample form as a result of the selective vaporization, and a series of irradiations to a deeper layer creates a stationary state for forming fine particles having the same composition as the mother specimen. That is, the surface of the irradiated trace has a different composition to the mother specimen, whereas the composition of fine particles formed by laser irradiation in the same section are identical to that of the mother specimen. In order to practically achieve such a series of irradiations, the irradiation energy density from each pulse must be high enough to vaporize all the components, and pulse irradiation must be repeated at a high frequency to shorten the analysis time.

In line and dot irradiation methods, since a melted section having a different concentration migrates and solidifies on the side faces due to the pressure caused by vaporization, an entire section having a different concentration cannot be vaporized by the next laser irradiation. Therefore, the composition of the fine particles is significantly affected by the selective vaporization because a series of irradiations leaves sections having different compositions from the mother specimen. The section with varied concentration can be completely vaporized by repeated irradiation over the same region and a stationary state in which the composition of the mother specimen is the same as that of the fine particles can be achieved. The effect of an edge having a different concentration is negligible by optimizing the size of the irradiated region, for example, by irradiating a size of at least ten fold of the spot diameter of a single pulse.

The number of repeated irradiation cycles on the same point in laser vaporization analysis will now be theoretically discussed.

A concentration $C_0$ of a given element in the mother specimen and a concentration $C_{p1}$ of the fine particles formed during the first laser irradiation are assumed. When the selective vaporizaion ratio is m under the given irradiation conditions, the concentration of the fine particles is expressed as $C_{p1}=m_{C0}$. Vaporization of a region having a depth d of the irradiated area S per laser irradiation is assumed.

Figure 2A:
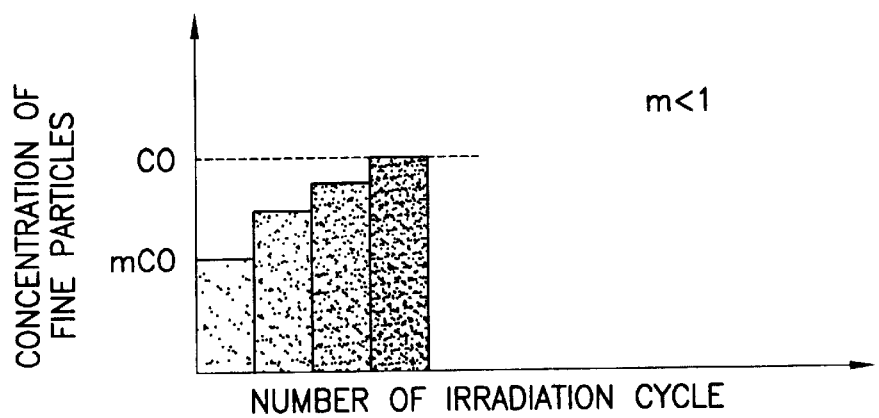
FIGS. 2A and 2B are graphs illustrating the correlations between irradiation cycle number and the concentration of fine particle, and between the depth and the concentration of the mother specimen, when the selective vaporization ratio m is less than 1.
Figure 2B:
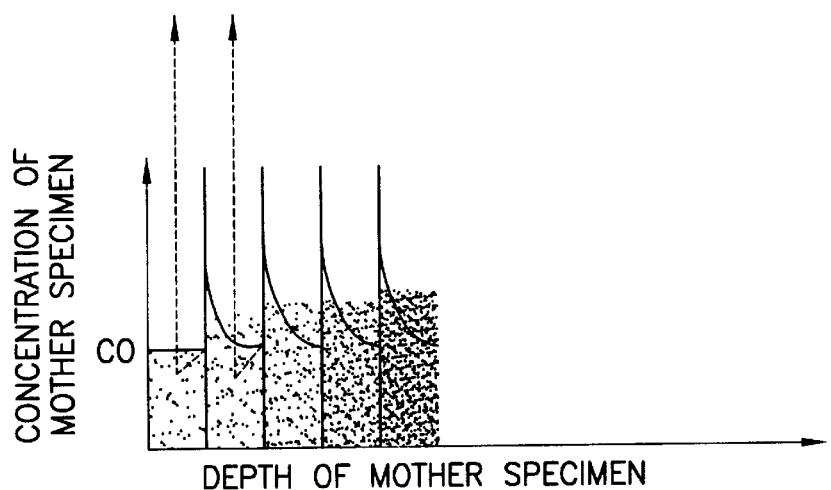

(1) When m<1, or when the elemental concentration in the fine particles is lower than that in the mother specimen (refer to FIG. 2):

Since the non-vaporized part with a concentration of $C_0-C_{p1}$ is accumulated onto the surface of the specimen after the first irradiation step, the surface concentration C1 is expressed as follows:

$$C_1 = C_0 + (C_0 - C_{p1}) = C_0\{1 + (1-m)\} \quad (2)$$

Thus, the concentration $C_{p2}$ of the fine particles which are formed during the second irradiation step on the same surface is as follows:

$$C_{p2}=mC_1=C_0\times m\times\{1+(1-m)\}$$

and thus the surface concentration $C_2$ is as follows:

$$C_2=C_0+(C_1-CP_2)=C_0[1+1+(1-m)-m\{1+(1-m)\}]=C_0[1+(1-m)+(1-m)^2]=C_0\{1-(1-m)^3\}/m \quad (3)$$

Thus, the concentration $C_{p3}$ of the fine particles which are formed during the third irradiation step on the same surface is as follows:

$$C_{Cp3}=C_0\{1-(1-m)^3\}$$

Similarly, the concentration of $C_{PN}$ of the fine particles which are formed during the n-th irradiation step on the same surface is as follows:

$$C_{PN}=C_0\}1-(1-m)^n\} \quad (4)$$

The above equation (4) demonstrates that the concentration of the fine particles approaches the concentration $C_0$ of the mother specimen as the number n of irradiation increases, when m>0, that is, when the condition that all the elements can vaporize is satisfied. Further, the equation (4) illustrates that the selective vaporization ratio of the first laser irradiation determines the number of irradiation cycles at which selective vaporization does not occur. For example, the number of irradiation cycles necessary to suppress the relative difference between the concentrations of the fine particles and mother specimen to 5% or less is two when the selective vaporization ratio is 0.9, five when the ratio is 0.5, or 30 when the ratio is 0.1.

(2) When m>1, or when the elemental concentration in the fine particles is higher than that in the mother specimen (refer to FIG. 3):

The element migrates into the surface layer by diffusion from inside the melted section of the mother specimen and the like, and vaporizes from the surface. Thus, the concentration of the element at the surface is reduced after irradiation. The decrease in concentration is compensated by diffusion from the inside during the second and following irradiation steps. The number of irradiation cycles needed to reach the stationary state depends on the laser irradiation conditions. In the present invention, since the concentration gradient is large due to a short, high-power input, the diffusible layer is narrow. Thus, the stationary state is attained after the second irradiation step.

FIG. 1 is a block diagram illustrating an apparatus configuration in which a laser vaporization analytical method in accordance with an embodiment of the present invention is applied. In this apparatus, electrical power is supplied from an electric laser 1 to a solid-state laser rod 2. The solid-state laser rod 2 is excited and oscillated by means of a power supply. Electrical energy is supplied to an electrical power source for laser excitation such as a lamp or a semiconductor laser provided near the solid-state laser rod 2 in order to excite the light source, and the laser beam is oscillated by means of the pumping light. Alternatively, the pumping light may be supplied to the solid-state laser rod 2 through an optical fiber or the like. The laser beam emitted from the solid-state laser rod 2 is oscillated in a Q-switch element 3 to generate high-energy laser pulses.

The resulting laser pulses are radiated onto two scanning mirrors 5 and 6 via a beam expander 4 and reflected toward the focal point of a condenser lens 7. The position of the focal point and the optical path are two-dimensionally varied with the reflection angles of the scanning mirrors 5 and 6. The diameter of the focused beam depends on the optical characteristics of the laser beam and the focal length of the condenser lens. When the focal length has a distance sufficient for the placement of an analytical cell, a high laser energy density may not be achieved due to the large diameter of the focused beam. In this case, the energy density of the radiated laser beam is adjusted so as to satisfy the threshold value by changing the magnification of the beam expander 4 to reduce the diameter, or lowering the frequency of the laser pulse to raise the energy per pulse.

A specimen 20 comes in close contact with an analytical cell 8 through an 0-ring 9 which prevents the leakage of gaseous argon supplied to the analytical cell 8. Other means such as a metallic mechanical seal or silicone rubber can be used instead of the 0-ring 9. When the specimen is small, the specimen is placed into a container and a structure for preventing the argon leakage between the container and the analytical cell 8 may be used.

The scanning frequencies of the scanning mirrors 5 and 6 are determined in view of the diameter of the radiated laser beam, the irradiated region and the frequency of the Q-switch. Because the track of the irradiated region is determined by the ratio of the scanning frequencies, one of the scanning mirrors 5 and 6 is swung at a relatively higher frequency of several dozen Hz or more and the other is swung at a lower frequency of several Hz or less or at a frequency having a difference within several Hz from the higher frequency (for example, 80:1 or 80:79).

Fine particles formed during laser irradiation are transferred to an analyzer 12 while being carried in gaseous argon, and introduced to the analytical cell 8 from an argon source 10 through a transfer pipe 11 for analysis. The inner diameter of the transfer pipe 11 is preferably 2 mm$\phi$ or more, and the flow rate of gaseous argon is preferably 0.2 liter/min. A suitable quantity of the fine particles are supplied to the analyzer depending on the characteristics of the analyzer. In ICP (inductively coupled plasma) emission spectrometry, a suitable quantity of the fine particles is 1 $\mu$g/sec. or more. When the carbon content in a steel is determined, a larger amount of fine particles is preferably supplied in view of the carbon contamination of gaseous argon. In contrast, in ICP-MS (inductively coupled plasma mass spectrometry), satisfactory results are obtainable with a smaller quantity of fine particles. The fine particles transferred to the analyzer 12 are vaporized and decomposed in the analyzer for analysis based on the procedure inherent in the analyzer. The results of elemental analysis can be obtained in such a manner.

Table 1 shows $\alpha$ values on the threshold of the fine particles forming condition during laser irradiation regarding typical metallic elements.

TABLE 1

| Element | $\alpha$ |
|---------|----------|
| Fe | 3,000 |
| Zn | 1,500 |
| Cu | 3,400 |
| W | 6,000 |
| Ti | 3,000 |
| Al | 1,900 |
| Al$_2$O$_3$ | 6,000 |

Figure 4:
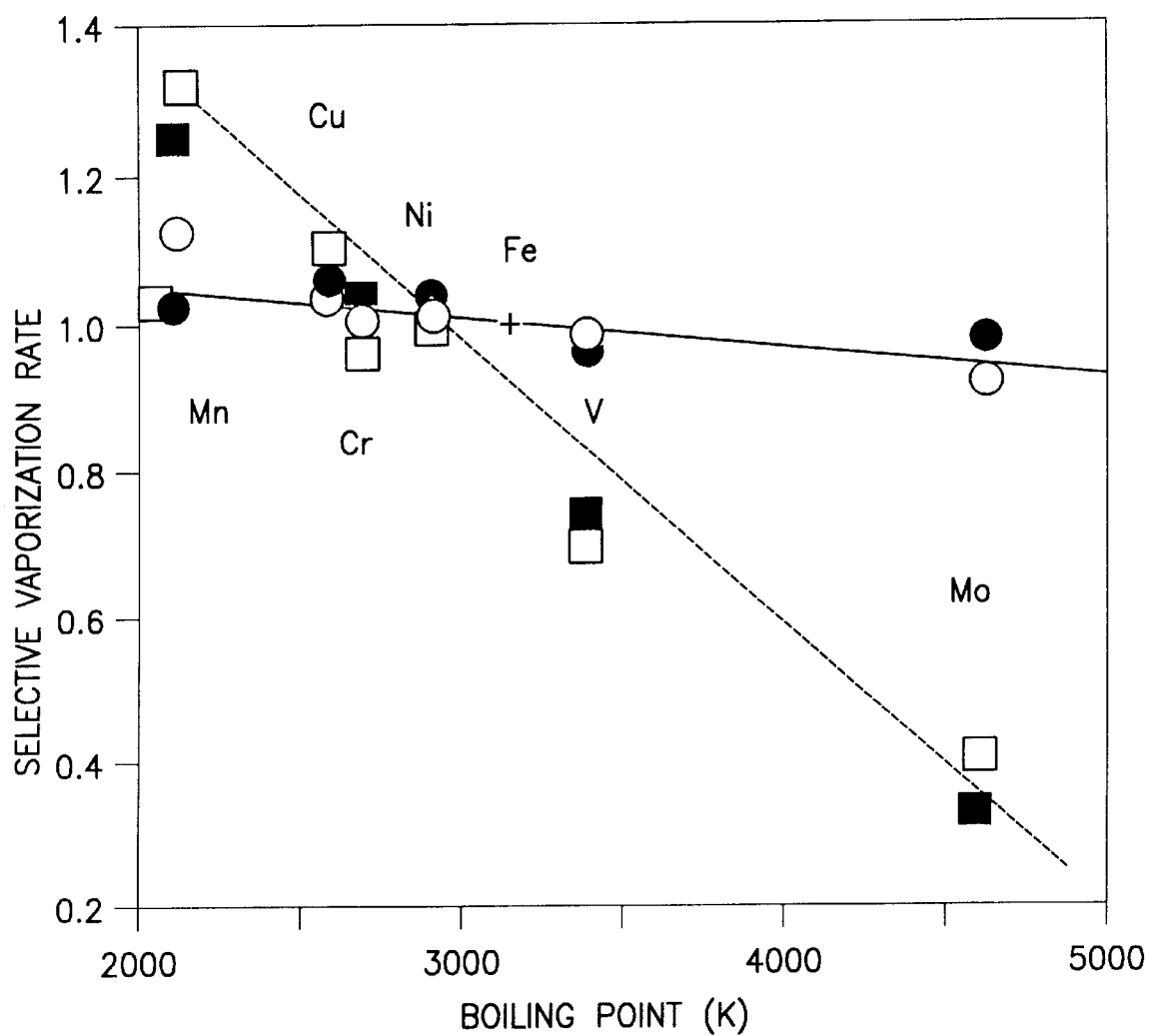
FIG. 4 is a graph illustrating the correlation between the selective vaporization ratio of fine particles and the boiling point of each element in a metallic specimen.

FIG. 4 is a graph illustrating the correlation between the selective vaporization or collection ratio of fine particles and the boiling point of each element in a metallic specimen. When fine particles are formed by line scanning, the vaporization ratio noticeably changes with a high correlation to the boiling point. In contrast, in the laser irradiation method in accordance with the present invention, the selective vaporizaion ratio is nearly equal to 1, and does not substantially change.

Table 2 shows comparative data for accuracies of laser ICP analysis using various irradiation methods. Table 2 demonstrates the following results:

A: Repeated irradiation of the same surface in accordance with the present invention gives small relative standard deviations of less than 1%;

B: Single scan planer irradiation, in which one of the scanning mirrors is rapidly scanned while the other mirror is unidirectionally scanned to radiate the laser beam onto the same surface area as in method A, has inferior deviations to method A due to the selective collection of fine particles; and C: Line scan irradiation gives poor results due to the small amount of fine particles collected.

TABLE 2

| | Relative Standard Deviation (%) | | | | |
|---|---|---|---|---|---|
| | Si | Mn | Cu | Al | Cr |
| A: Repeated Irradiation | 0.63 | 0.62 | 0.59 | 0.55 | 0.32 |
| B: Single Scan Irradiation | 1.4 | 1.2 | 1.5 | 1.2 | 0.9 |
| C: Line Scan Irradiation | 2.3 | 3 | 3.4 | 4.1 | 1.8 |

Table 3 shows typical examples of laser irradiation conditions.

TABLE 3

| | Lamp Excited Laser | LD Excited Laser |
|---|---|---|
| Laser Rod | Nd:YAG | ND:YVO$_4$ |
| Laser Wavelength | 1.064 µm | 1.064 µm |
| Pumping Source | Kr-arc lamp | Laser diode |
| Optical System for Oscillation | Horizontal | Vertical |
| Beam Mode | Multi mode | Single mode |
| Q-Switch System | Acoustooptic | Acoustooptic |
| Frequency | 1 kHz | 50 kHz |
| Pulse Half-Width | 110 nsec. | 20 nsec. |
| Pulse Energy | 10 mJ | 0.1 mJ |
| Scanning System | Two galvano-mirrors | Two galvano-mirrors |
| Beam Expander | x3 | x3 |
| Focal Distance | 100 mm | 100 mm |
| Diameter of Focused Laser Beam | 230 µm | 50 µm |

In accordance with a laser vaporization analyzer of an embodiment of the present invention, a laser beam from a laser oscillation section is radiated onto a solid specimen in an inert carrier gas stream, and a part of the solid specimen is collected as fine particles. The fine particles are transferred to a detector for elemental analysis. The laser oscillation section is provided with a semiconductor laser which emits pumping light.

In accordance with a laser vaporization analyzer of another embodiment of the present invention, the laser oscillation section is provided with a semiconductor laser which emits pumping light, a laser rod of which one end receives and amplifies the laser beam from the semiconductor laser, and resonators provided at both ends of the laser rod.

In accordance with a laser vaporization analyzer of a further embodiment of the present invention, a semiconductor laser emits a laser beam as a pumping source, the laser beam is optically amplified and resonated, and the optically amplified laser beam is irradiated onto a solid specimen. Since a semiconductor laser is used as a pumping light source, the laser oscillation section can be miniaturized and simplified compared to conventional kr-arc lamps. The pumping laser beam from the semiconductor laser is radiated onto one end of the laser rod and optically amplified as a single mode oscillation. Since the optically amplified laser beam is highly coherent, the diameter of the laser beam radiated onto the specimen can be decreased, resulting in increased energy density. Such a vertical mode oscillation using a semiconductor laser enables the laser rod to be shorter and the resonator configuration to be simplified.

In accordance with a laser vaporization analyzer of another embodiment of the present invention, a laser oscillation section is further provided with an optical transfer cable for connecting a semiconductor laser and a laser rod.

In accordance with a laser vaporization analyzer of a still further embodiment of the present invention, a semiconductor laser is connected to a laser rod through an optical transfer cable, so that a laser beam from the semiconductor laser is introduced to the laser rod through the optical transfer cable. Since the semiconductor laser as a pumping light source is separated from the laser rod in this configuration, the head section including the laser rod can be further miniaturized and simplified.

Figure 5:
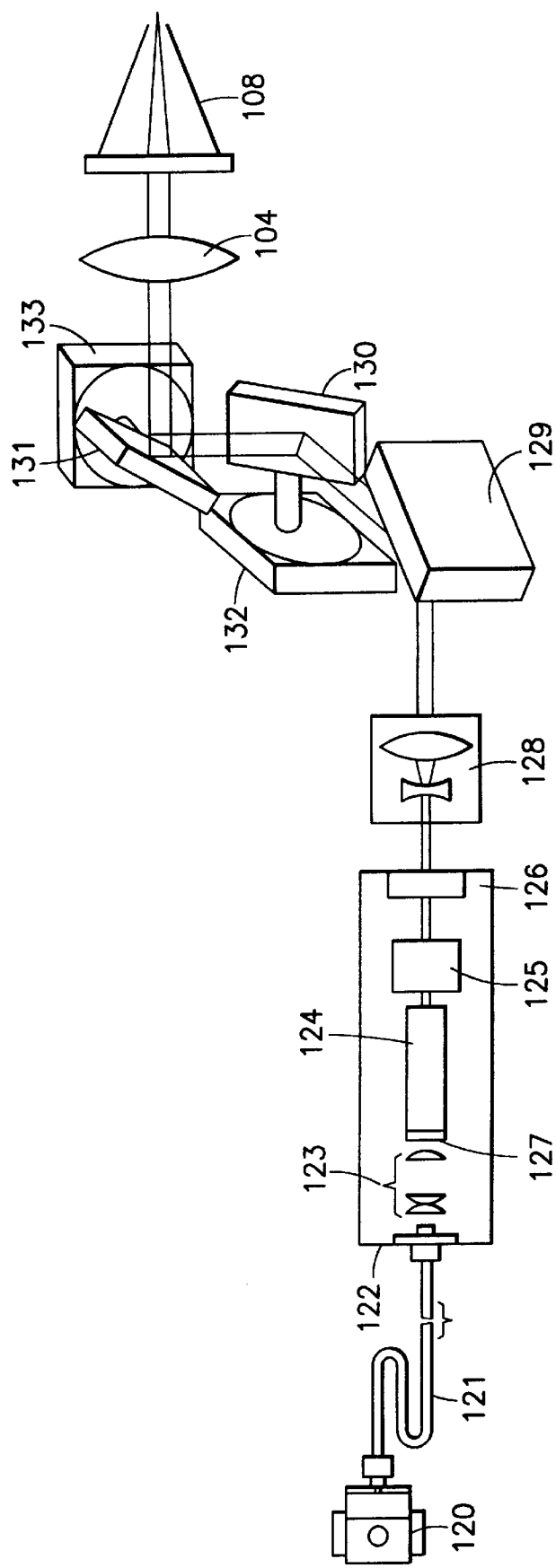
FIG. 5 is a block diagram illustrating a configuration of a laser oscillating section used in a laser vaporization analyzer in accordance with an embodiment of the present invention.
Figure 6:
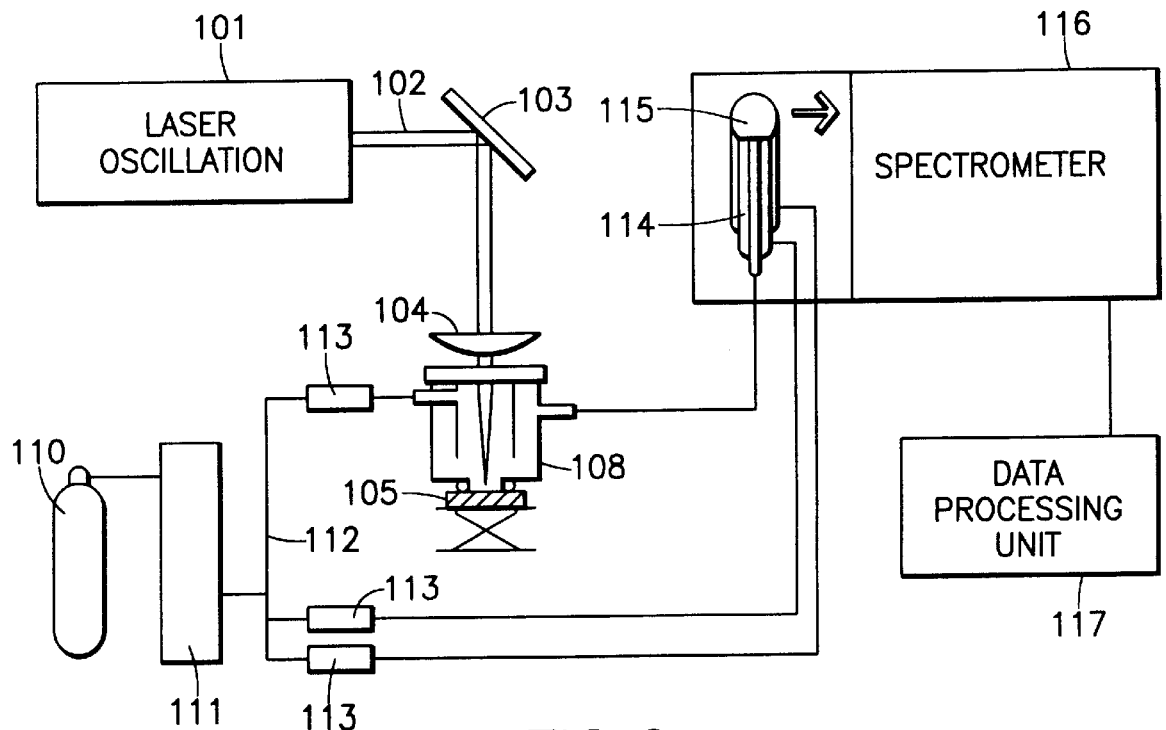
FIG. 6 is a block diagram illustrating an overall configuration of a laser vaporization analyzer in accordance with an embodiment of the present invention.

FIG. 6 is a block diagram illustrating an overall configuration of a laser vaporization analyzer in accordance with an embodiment of the present invention. The laser beam 102 oscillated in the laser oscillation section 101 is converged with a condenser lens 104 while adjusting the direction of the beam with a rotation mirror 103 and is radiated onto a solid specimen 105. The rotating mirror 103 is rotated by a rotation mechanism as set forth below (refer to FIG. 5), and the condenser lens moves by a parallel moving mechanism (not shown in the figure). The solid specimen 105 is placed inside an irradiation cell 108, while supplying a carrier gas. The carrier gas from a cylinder 110 is purified through a purifier 111 according to demand before the carrier gas is supplied to the irradiation cell 108 and a high-frequency plasma torch 114 as the carrier gas or flame gas via a pipe 112. A Zr-getter-type purifier is used in this embodiment. The pipe 112 is provided with a flow rate regulator 113 to adjust the flow rate of the carrier gas. Since a stainless steel pipe is used as the pipe 112, and the irradiation cell 108 and the plasma torch 114 are made of glass, a sealable material such as an 0-ring is used for the connection between them.

Fine particles are formed by radiation of the laser beam 102 onto the solid specimen 105 and transferred to the plasma torch 114 with the carrier gas. The fine particles in the plasma torch 114 are decomposed and excited by Ar plasma, and light having a spectra inherent to individual elements is emitted in response to the composition of the fine particles. The intensity of emitted light from each element is determined with a spectrometer 116, and the composition of the specimen is determined with a data processing unit 117 using a previously determined calibration curve.

FIG. 5 is a block diagram illustrating a configuration of the laser oscillating section 101 set forth above. The output of the semiconductor laser 120 pumping source is introduced inside the laser head 122 through an optical fiber 121. The laser beam introduced inside the laser head 122 enters one end of a YAG laser rod 124 through a condenser lens 123 and is optically amplified. A Q-switch 125 and an output mirror 126 are provided at the emitting end of the YAG laser rod 124, and a reflective film 127 is provided at the incident end of the YAG laser rod 124. The reflective film 127 (which transmits, for example, light of 0.80 µm and reflects light of 1.064 µm) and the output mirror 126 form a resonator which amplifies the energy of the incident laser from the semiconductor laser 120 by resonance and emits the amplified laser beam to a beam expander 128.

The laser beam diameter is expanded in the beam expander 128 and is introduced to an irradiation cell 108 through a 45-degree reflective mirror 129, a scanning mirror A 130, a scanning mirror B 131, and a condenser lens 104. The 45-degree reflective mirror 129, scanning mirror A 130 and scanning mirror B 131 correspond to the rotation mirror 103 in FIG. 5. The positions of the scanning mirror A 130 and scanning mirror B 131 are adjusted with ultrasonic motors 132 and 133 to scan the laser beam radiated onto a solid specimen 105 placed inside the irradiation cell 108.

The laser oscillating section in FIG. 5 uses a semiconductor laser 120 having a high laser oscillation efficiency as a pumping source. In conventional lamp methods, part of the continuous light emitted from a lamp is absorbed. In contrast, a laser beam having a high absorption coefficient for a specified wavelength (for example 0.81 $\mu$m) can be emitted from the semiconductor laser 120 with a high laser oscillation efficiency. Since a smaller capacity power source (e.g. 100 V) is usable without cooling water, a compact and light apparatus can be fabricated. The semiconductor laser 20 used in this embodiment is of Ga-As-type, a laser beam of 809 nm and 20 W can be emitted using 100 V of electrical power. Since the semiconductor laser 120 in the laser oscillation section is separated from the laser head 122 and connected to it through the optical fiber 121, a more compact and light laser head 122 (e.g. 1.5 Kg) suitable for handling can be achieved. A typical conventional laser head (e.g. 22 Kg) requires a turn table to move it.

The pumping light radiated into one end of the YAG laser rod 124 from the semiconductor laser 120 is optically amplified by vertical oscillation (the pumping light is radiated onto the side face of the rod). Thus, the oscillation is carried out as single mode oscillation. Since the optically amplified laser beam is highly coherent, the diameter of the laser beam radiated onto the specimen can be decreased, resulting in increased energy density (for example, 45 $\mu$m is the diameter in this embodiment whereas 230 $\mu$m in conventional methods). Such a vertical mode oscillation using a semiconductor laser enables the laser rod to be shorter and the resonator configuration to be simplified.

In this embodiment, a laser beam with a short pulse width is radiated using the Q-switch 125 in order to enhance the radiation energy onto the solid specimen 105 (for example, 10 nsec. to 100 nsec. in conventional methods). Further, the diameter of the radiated laser beam is focused. The laser head 120 can emit a laser beam having an average power output of 4 W, a pulse width of 10 nsec. and a pulse frequency of 50 KHz.

Additionally, in order to increase the number of the fine particles formed, the laser beam is scanned with the scanning mirrors A 130 and B 131 to spread the track of the irradiated region and thus to promote formation of the fine particles. At the same time, the frequency of the laser pulse is raised, for example, 1 kHz to 50 kHz to effectively use the energy for vaporization.

Figure 7:
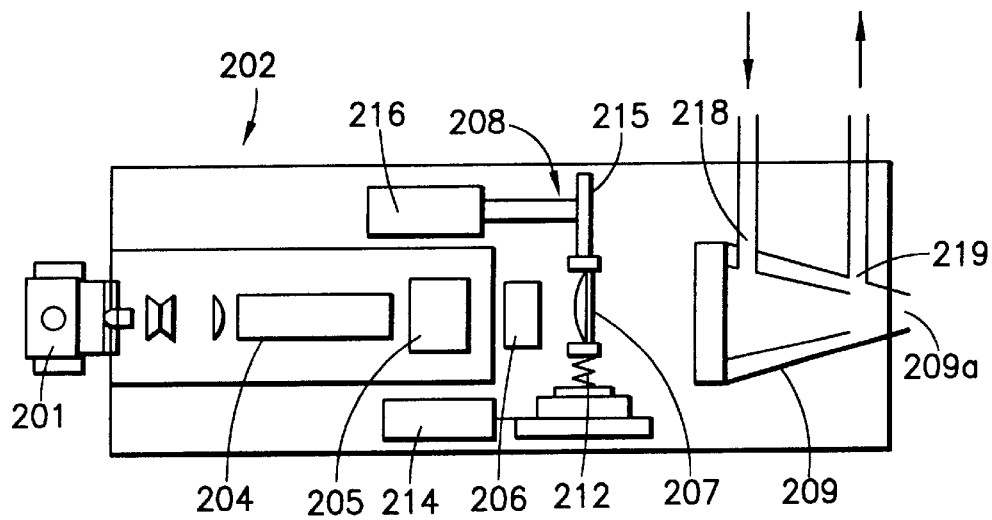
FIG. 7 is an outlined schematic view of an embodiment of an apparatus in accordance with the present invention.
Figure 8:
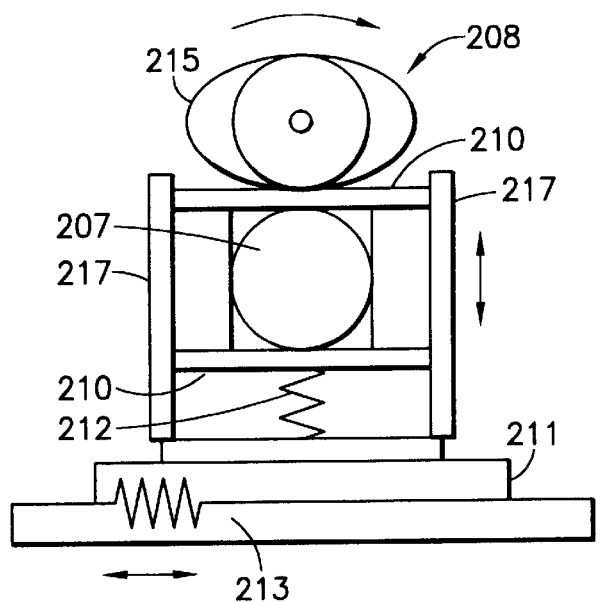
FIG. 8 is an outlined front view of a lens swinging mechanism.

FIG. 7 is an outlined schematic view of an embodiment of an apparatus in accordance with the present invention, and FIG. 8 is an outlined front view of a lens swinging mechanism. As shown in FIG. 7, the apparatus comprises a semiconductor laser oscillator 201 and a laser irradiation head 202 provided with the semiconductor laser oscillator 201. The laser irradiation head 202 is provided with a laser oscillation section comprising a YAG rod 204 as a solid laser medium and a Q-switch 205, which continuously oscillates a W-switch laser beam using pumping light from the semiconductor laser oscillator 201. The laser irradiation head 202 is further provided with a beam expander 206, a condenser lens 207, a lens swinging mechanism 208 and a cell 209 to converge the laser beam from the laser oscillation section on the surface of the specimen to be analyzed.

As shown in FIGS. 7 and 8, the condenser lens 207 is supported with a frame 210 which is vertically movably attached between two vertical props 217 on a table 211 via a spring 212. The lens swinging mechanism 208 comprises a horizontal lens moving mechanism which reciprocally moves the table 211 with the frame 210 supporting the condenser lens 207 along the horizontal direction perpendicular to the laser beam for a given amplitude, and a vertical lens moving mechanism which reciprocally moves the frame 210 of the condenser lens 207 along the vertical direction perpendicular to the laser beam for a given amplitude.

The horizontal lens moving mechanism comprises a feed screw 213 which is engaged with a rack formed on the side of the table 211, and a reversible motor 214 to rotate the feed screw 213. The table 211 with the condenser lens 207 and the frame 210 reciprocally moves in the horizontal direction perpendicular to the laser beam for a given amplitude by means of forward or reverse rotation of the feed screw 213 driven by the reversible motor 214.

The vertical lens moving mechanism comprises a cam 215 attached with the top face of the frame 210 and a motor 216 to rotate the cam 215. A spring 212 is provided between the bottom face of the frame 210 and the table 211. The condenser lens 207 reciprocally moves with the frame 210 in the vertical direction perpendicular to the laser beam for a given amplitude by means of rotation of the cam 215 driven by the motor 216.

The cell 209 is provided with an inert gas inlet 218 to feed inert gas such as gaseous argon from an inert gas generator (not shown in the figure), and a transfer port 219 to transfer the fine particles formed by laser irradiation in the inert gas. The fine particles are transferred to an ICP (inductively coupled plasma) spectrometer (not shown in the figure) by a carrier gas through a pipe connected to the transfer port 219.

After the energy density of the laser beam, which is excited by the semiconductor laser oscillator 201 and oscillated by the YAG rod 204, is enhanced by the Q-switch element 205, the laser beam is converged by the condenser lens 207 and radiated onto the surface of the metallic specimen through the cell 209. When the condenser lens 207 is swung along the vertical and horizontal directions perpendicular to the laser beam for a given amplitude by means of the lens swinging mechanism 208 comprising the horizontal and vertical lens moving mechanisms, the focal point of the laser beam moves along the metallic specimen irradiated through the cell 209 to draw a plane. Thus, fine particles on the plane surface vaporize. The vaporized fine particles are transferred to the ICP spectrometer with the inert gas for analysis. Thus, metallic materials can be rapidly and accurately analyzed with no preparatory procedures such as cutting regardless of its shape and temperature.

Since the semiconductor laser oscillator 1 is used for the pumping light source in the apparatus in accordance with the present invention, no water cooling process is needed unlike the conventional Kr-arc lamp source. Thus, a compact, light apparatus can be fabricated and can operate with low electric power. Further, the apparatus has a high laser excitation efficiency because the semiconductor emits light of a specified wavelength having a high absorbance.

It is preferable that the surface area which is irradiated with the focused laser beam be at least 1 mm$^2$. An area of less than 1 mm$^2$ may decrease analytical reliability due to segregation. The minimum moving rate of the focused laser beam is determined in view of the diameter of the focused laser beam, pulse frequency and energy per pulse.

Figure 9:
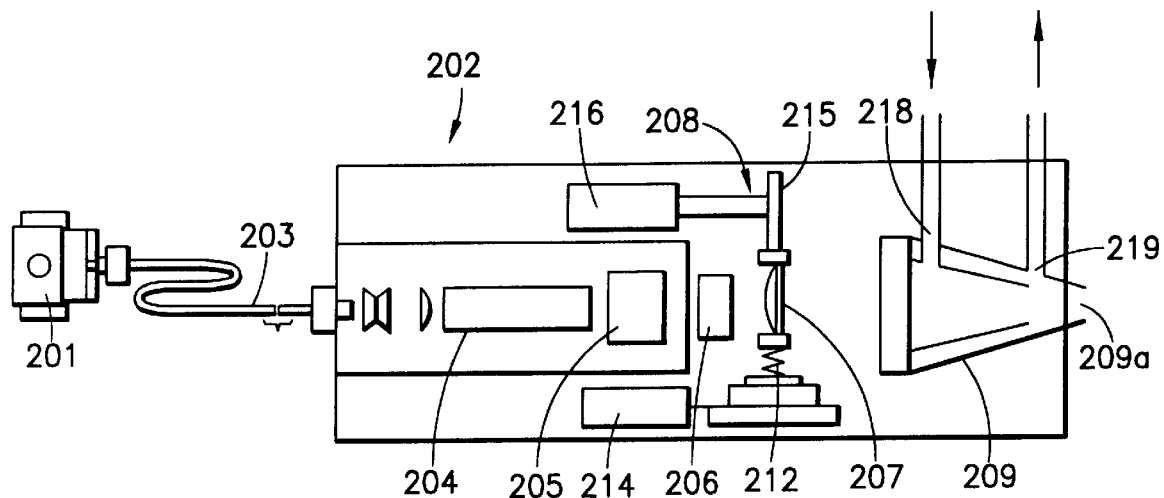
FIGS. 9 through 13 are outlined schematic views of other embodiments of the apparatus in accordance with the present invention.

FIG. 9 is an outlined schematic view of another embodiment of the apparatus in accordance with the present invention. A semiconductor laser oscillator 201 is separately provided with a laser irradiation head 202 and is connected to the laser irradiation head 202 through a light transfer cable 203 such as optical fiber cable. Thus, the laser irradiation head 202 can be further miniaturized and be easily handled during analysis.

The components of a high temperature piece of steel was determined using an apparatus having the following specifications as shown in FIGS. 7 and 9:

Pumping light source: Semiconductor laser oscillator (wavelength: 817 nm)

Laser: Nd-YAG laser with ultrasonic Q-switch (wavelength: 1.06 μm)

Carrier gas: argon

Analyzer: ICP emission spectrometer

After the analytical surface of the steel was ground, the irradiation port 209a of the irradiation cell 209 came in close contact with the analytical surface. Laser beam pulses having a frequency of 50 KHz and an average power output of 10 W were radiated from the semiconductor oscillator 201 onto the analytical surface of the steel, while the condenser lens was swung with the lens swinging mechanism 208 in the vertical and horizontal directions perpendicular to the laser beam so that an area of 3 mm$^2$ on the surface was irradiated with the focused laser beam. The fine particles vaporized from the analytical surface were transferred to the ICP spectrometer with the argon carrier gas.

The fine particles were directly excited and emitted light in the ICP spectrometer under the following conditions; frequency: 27 MHz, output energy: 1.3 KW, plasma gas flow rate: 15 liter/min., auxiliary gas flow rate: 1 liter/min. and carrier gas flow rate: 1 liter/min. Each component was determined with a spectrometer. The composition of the steel was determined accurately and stably in an extremely short time period, i.e., 30 seconds.

The apparatus is illustrated with reference to FIG. 10. A laser irradiation head 302 comprises a semiconductor laser oscillator 301, a laser converging mechanism 308 , and a laser irradiation cell 315. The laser irradiation head 302 is further provided with a YAG rod 304 as a solid-state laser medium, a Q-switch element 305, a condenser lens 306 and an output mirror 307. The YAG rod 304 and the Q-switch element 305 composes a laser oscillation section for continuously oscillating Q-switch laser light by the pumping light from the semiconductor laser.

The laser converging mechanism 308 comprises a fixed reflective mirror 309, a first scanning mirror 311 and a second scanning mirror 312 which reciprocally rotate within a given angle by ultrasonic motors 310 and 310' respectively, and a condenser lens 313. The first and second scanning mirrors 311 and 312 are vertically placed each other. A beam expander 314 is provided between the laser irradiation head 302 and the laser converging mechanism 308. The beam expander 314 comprises convex and concave lenses and expands the beam diameter to increase the converging characteristics.

After the energy density of the laser beam which is excited by the semiconductor laser oscillator 301 and is oscillated from the YAG rod 304 is enhanced with the Q-switch element 305, the diameter of the laser beam is expanded with the beam expander 314. The laser beam is deflected 40 degrees with the reflective mirror 309 and is irradiated to the laser converging mechanism 308.

In the laser converging mechanism, the laser beam is swung with the first scanning mirror 311 driven by the ultrasonic motor 310 in the horizontal direction perpendicular to the laser beam for a given amplitude. The horizontally swung laser beam is swung with the second scanning mirror 312 driven by the ultrasonic motor 310' in the vertical direction perpendicular to the laser beam for a given amplitude.

The horizontally and vertically swung laser beam is converged through the condenser lens 313 and irradiated onto the surface of the analytical metallic specimen through the laser irradiation cell 315. The focal point of the laser beam moves on the metallic specimen to draw a plane. Thus, fine particles in the plane surface vaporize.

The laser irradiation cell 209 is provided with an inert gas inlet 316 to feed inert gas such as gaseous argon from an inert gas generator (not shown in the figure), and a transfer port 317 to transfer the fine particles formed by laser irradiation with the inert carrier gas. The fine particles is transferred for analysis to an ICP (inductively coupled plasma) analyzer (not shown in the figure) with the inert carrier gas through a pipe connected to the transfer port 317.

Since the semiconductor laser oscillator 301 is used for the pumping light source in the apparatus in accordance with the present invention, no water cooling process is needed unlike the conventional Kr-arc lamp source. Thus, a compact, light apparatus can be fabricated and can operate with low electric power. Further, the apparatus has a high laser excitation efficiency because the semiconductor emits light of a specified wavelength having a high absorbance.

Since the first and second scanning mirrors 311 and 312 in the laser converging mechanism 308 reciprocally rotate with ultrasonic motors 310 and 310', the operation can be smoothly achieved and the laser beam is correctly swung. Thus, metallic materials can be rapidly and accurately analyzed with no preparatory procedures regardless of its shape and temperature.

It is preferable that the surface area which is irradiated with the focused laser beam be at least 1 mm$^2$. An area of less than 1 mm$^2$ may decrease analytical reliability due to segregation. The minimum moving rate of the focused laser beam is determined in view of the diameter of the focused laser beam, pulse frequency and energy per pulse.

Figure 11:
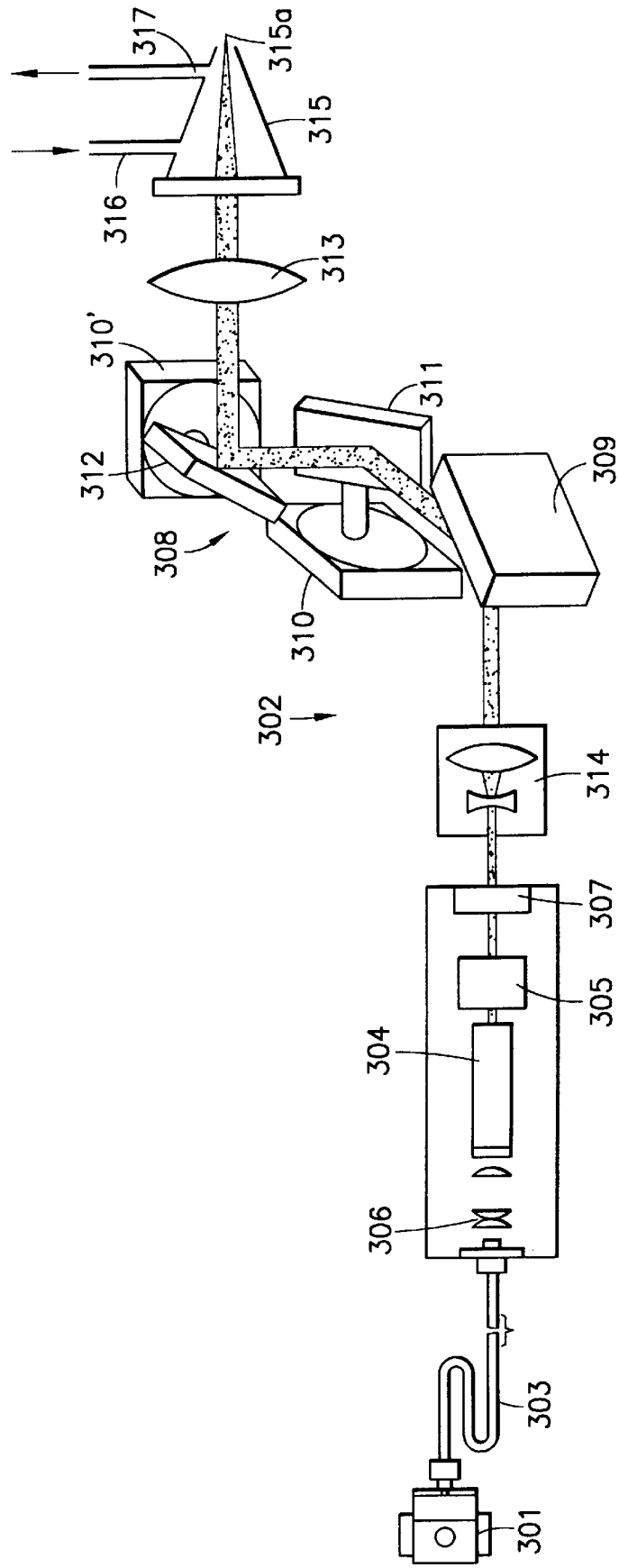

FIG. 11 is an outlined schematic view of another embodiment of the apparatus in accordance with the present invention. A semiconductor laser oscillator 301 is separately provided with a laser irradiation head 302 and is connected to the laser irradiation head 302 through a light transfer cable 303 such as optical fiber cable. Thus, the laser irradiation head 302 can be further miniaturized and be easily handled during analysis.

Figure 10:
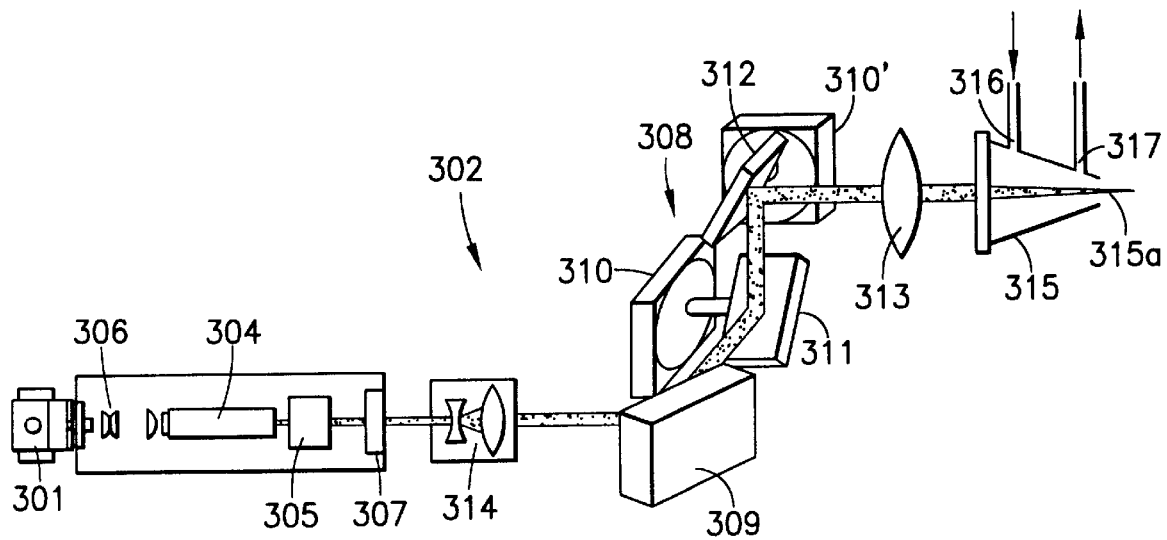

The components of a high temperature piece of steel was determined using an apparatus having the following specifications as shown in FIG. 10:

Pumping light source: Semiconductor laser oscillator (wavelength: 817 nm)

Laser: Nd-YAG laser with ultrasonic Q-switch (wavelength: 1.06 μm)

Carrier gas: argon

Analyzer: ICP emission spectrometer

After the analytical surface of the steel was ground, the irradiation port 315a of the irradiation cell 315 came in close contact with the analytical surface. Laser beam pulses having a frequency of 50 KHz and an average power output of 10 W were radiated from the semiconductor oscillator 1 onto the analytical surface of the steel, while the first and second scanning mirrors in the laser converging mechanism 308 were reciprocally rotated with the ultrasonic motors 310 and 310' respectively, so that an area of 3 mm² on the surface was irradiated with the focused laser beam.

The fine particles vaporized from the analytical surface were transferred to the ICP spectrometer with the argon carrier gas. The fine particles were directly excited and emitted light in the ICP spectrometer under the following conditions; frequency: 27 MHz, output energy: 1.3 KW, plasma gas flow rate: 15 liter/min., auxiliary gas flow rate: 1 liter/min. and carrier gas flow rate: 1 liter/min. Each component was determined with a spectrometer. The composition of the steel was determined accurately and stably in an extremely short time period, i.e., 30 seconds.

Figure 12:
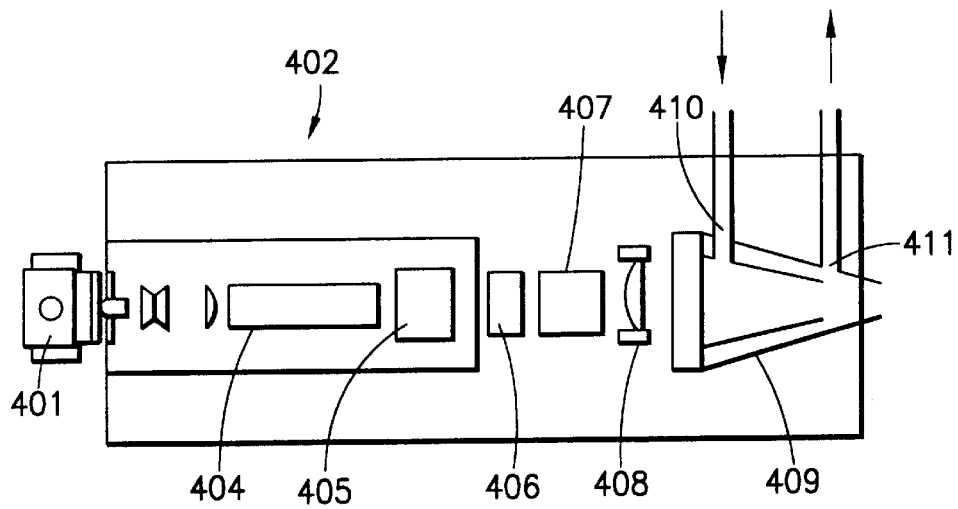

FIG. 12 is an outlined schematic view of another embodiment of the apparatus in accordance with the present invention. The apparatus comprises a laser irradiation head 402 attached with a semiconductor laser oscillator 401. The laser irradiation head 402 is further provided with a YAG rod 404 as a solid-state laser medium, a Q-switch element 405, a beam expander 406, an acoustooptic deflector 407, a condenser lens 408 and a cell 409. The YAG rod 404 and the Q-switch element 405 composes a laser oscillation section for continuously oscillating Q-switch laser light by the pumping light from the semiconductor laser. The beam expander 406 converges the laser beam onto the surface of the analytical specimen, and the acoustooptic deflector 407 swings the laser beam on the specimen surface for a given amplitude.

The laser irradiation cell 409 is provided with an inert gas inlet 410 to feed inert gas such as gaseous argon from an inert gas generator (not shown in the figure), and a transfer port 411 to transfer the fine particles formed by laser irradiation with the inert carrier gas. The fine particles is transferred for analysis to an ICP spectrometer with the inert carrier gas through a pipe connected to the transfer port 411.

In the acoustooptic deflector 407, when an ultrasonic wave propagates in a transparent medium, the refractive index of the medium periodically varies, and thus the light is phase-modulated in the medium to cause light diffraction. According to such an acoustooptic deflector 407, the laser beam is deflected so as to draw a plane and thus the focused laser beam can be swung at a high speed for a given amplitude.

The energy density of the laser beam which is excited by the semiconductor laser oscillator 401 and is oscillated from the YAG rod 404 is enhanced with the Q-switch element 405. The enhanced laser beam is deflected with the acoustooptic deflector 407 so as to draw a plane and irradiated onto the surface of the metallic material through the laser irradiation cell 409 such that the focused laser beam is swung for a given amplitude.

As a result, fine particles in the plane surface vaporize, and the fine particles is transferred to the ICP spectrometer with the inert carrier gas fed into the cell 409 for analysis. Thus, metallic materials can be rapidly and accurately analyzed with no preparatory procedures regardless of its shape and temperature.

Since the semiconductor laser oscillator 401 is used for the pumping light source in the apparatus in accordance with the present invention, no water cooling process is needed unlike the conventional Kr-arc lamp source. Thus, a compact, light apparatus can be fabricated and can operate with low electric power. Further, the apparatus has a high laser excitation efficiency because the semiconductor emits light of a specified wavelength having a high absorbance.

Further, since the laser beam is deflected with the acoustooptic deflector 407 so as to draw a plane, the focused laser beam can be smoothly swung during irradiation onto the surface of the metallic material through the laser irradiation cell 402.

It is preferable that the surface area which is irradiated with the focused laser beam be at least 1 mm². An area of less than 1 mm² may decrease analytical reliability due to segregation. The minimum moving rate of the focused laser beam is determined in view of the diameter of the focused laser beam, pulse frequency and energy per pulse.

Figure 13:
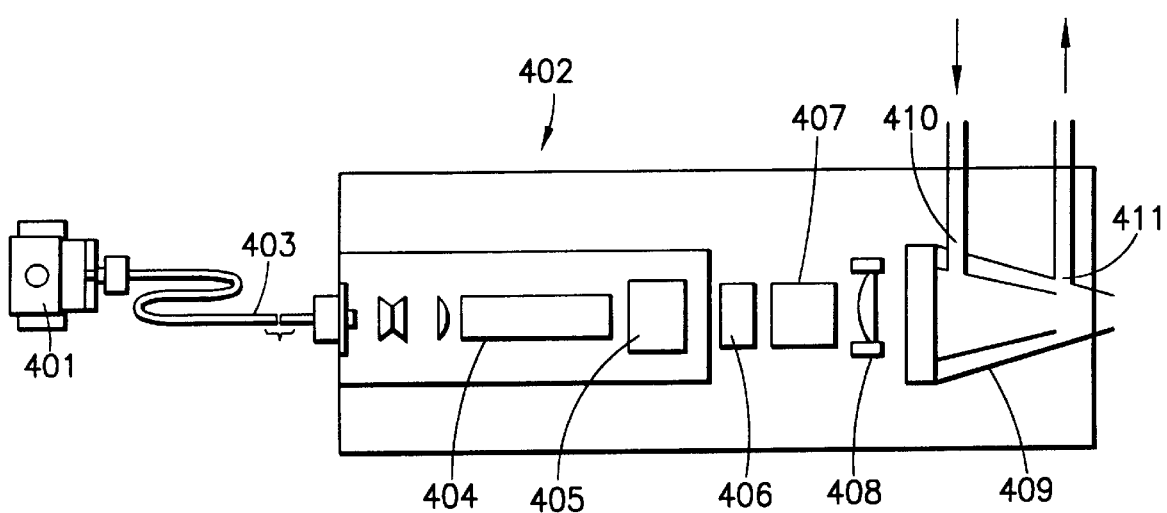

FIG. 13 is an outlined schematic view of another embodiment of the apparatus in accordance with the present invention. A semiconductor laser oscillator 401 is separately provided with a laser irradiation head 402 and is connected to the laser irradiation head 402 through a light transfer cable 403 such as optical fiber cable. Thus, the laser irradiation head 402 can be further miniaturized and be easily handled during analysis.

The components of a high temperature piece of steel was determined using an apparatus having the following specifications as shown in FIG. 12:

Pumping light source: Semiconductor laser oscillator (wavelength: 817 nm)

Laser: Nd-YAG laser with ultrasonic Q-switch (wavelength: 1.06 μm)

Acoustooptic deflector: Acoustooptic medium (single crystal $PbMoO_4$)

Carrier gas: argon

Analyzer: ICP emission spectrometer

After the analytical surface of the steel was ground, the irradiation port 409a of the irradiation cell 409 came in close contact with the analytical surface. Laser beam pulses having a frequency of 50 KHz and an average power output of 10 W were radiated from the semiconductor oscillator 401 onto the analytical surface of the steel, while swinging the laser beam with the acoustooptic deflector 407 in a plane, so that an area of 3 mm² on the surface was irradiated with the focused laser beam. The fine particles vaporized from the analytical surface were transferred to the ICP spectrometer with the argon carrier gas.

The fine particles were directly excited and emitted light in the ICP spectrometer under the following conditions; frequency: 27 MHz, output energy: 1.3 KW, plasma gas flow rate: 15 liter/min., auxiliary gas flow rate: 1 liter/min. and carrier gas flow rate: 1 liter/min. Each component was determined with a spectrometer. The composition of the steel was determined accurately and stably in an extremely short time period, i.e., 30 seconds.

Like aluminum in steel, some elements are present in different forms in steel, i.e., homogeneously dissolved in iron and of inhomogeneously distributed as compounds such as oxides. In such elements, the concentration distribution, as well as the concentration itself, offers meaningful information. However, conventional laser vaporization analysis does not offer such concentration distributions, but offers only the overall concentration.

In laser vaporization analysis in which converged laser pulses are radiated onto a specimen and the fine particles formed are transferred to the analyzer for determining the composition, if the analytical position is continuously moved in minute time periods to obtain momentary values, and if a series of momentary values are analyzed, the concentrations of an objective element in the homogeneously dissolved section and inhomogeneously precipitated section can be separately determined.

In laser vaporization analysis in accordance with the present invention, determination of the content of individual elements in the fine particles formed by laser irradiation is performed in a series of minute measuring times, while continuously moving the analytical position. Thus, each resulting value corresponds to an analytical value within the fine region defined by the minute time period.

Information on the overall concentration is obtainable with conventional determination techniques, whereas information on individual fine regions and on entire regions is obtainable with the present invention.

The movement of the laser beam is performed at a given rate to achieve a linear relation between the analytical position and time. Thus, it is preferable that the rate is constant. At the same time, the depth at which fine particles are formed and can be controlled by the movement rate.

In a graph illustrating momentary values varying with the minute measuring times, if the specimen consists of only a homogeneously dissolved section, the graph is linear and flat. If the fine particles are from an inhomogeneously precipitated section, a specified element exhibits a higher concentration in the respective momentary values.

Figure 16:
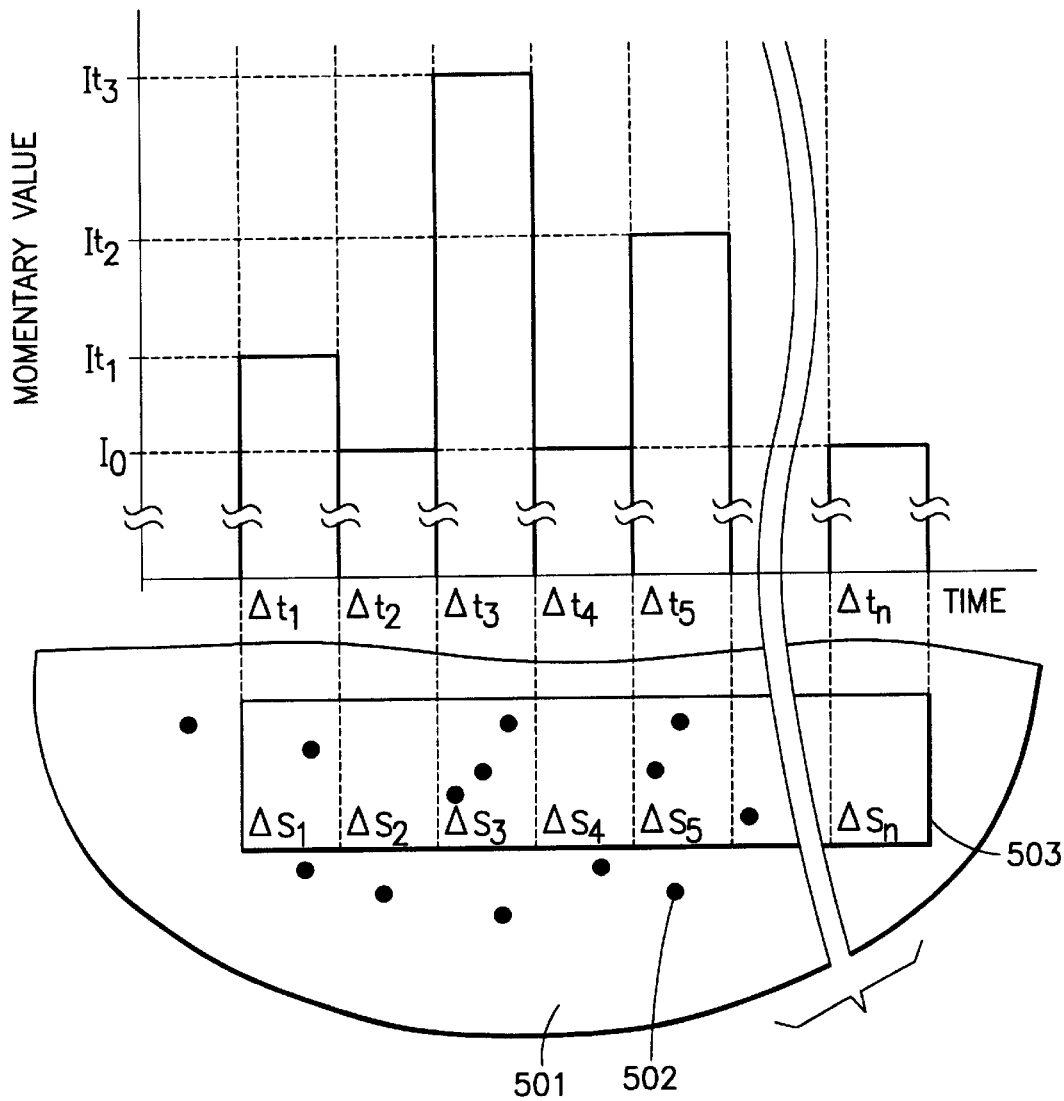
FIG. 16 is a schematic view illustrating momentary values at individual minute measuring times in an inhomogeneously precipitated section.

The principle for discriminating the homogeneously dissolved section from the inhomogeneously precipitated section will be illustrated with reference to FIG. 16 which is a schematic view illustrating momentary values at individual minute measuring times in an inhomogeneously precipitated section, in which numeral 501 represents a specimen, 502 represents an inhomogeneously precipitated section, and 503 represents an analytical region. The horizontal axis of the graph represents minute measuring times which reflect the individual irradiated positions shown below in the figure, and the vertical axis represents emission intensity at each minute measuring time which corresponds to the concentration of the objective element.

During a minute measuring time $\Delta t$, the specimen in the fine region $\Delta s$ is vaporized into fine particles while the position being irradiated with the laser beam moves. The inhomogeneously precipitated section included in the fine region $\Delta s$ is simultaneously vaporized to fine particles as with the homogeneously dissolved section. When a part of the objective element forms, the inhomogeneously precipitated section 502 and the balance of the objective element is dissolved in the main constituent element, the concentration of the objective element is higher in the inhomogeneously precipitated section than in the homogeneously dissolved section. Thus, fine particles from fine regions $\Delta s_2$, $\Delta s_4$ and $\Delta s_n$ not including the inhomogeneously precipitated section 502 have the composition of the homogeneously dissolved section, and emission intensities $It_2$, $It_4$ and $It_n$ corresponding to minute measuring times $\Delta t_2$, $\Delta t_4$ and $\Delta t_n$ are equal to $I_0$. On the other hand, when the inhomogeneously precipitated section 502 is included as in $\Delta s_1$, $\Delta S_3$ and $\Delta S_5$, the concentration of the objective element increases and the emission intensities $It_1$, $It_3$ and $It_5$ corresponding to minute measuring times $\Delta t_1$, $\Delta t_3$ and $\Delta t_5$ increase in response to the amount of the inhomogeneous precipitant. Thus, the homogeneously dissolved section and the inhomogeneously precipitated section can be separately determined by minute measuring time analysis.

In actual measurement, because $\Delta t$ is extremely short and does not have substantial width, a series of momentary values draw a waveform. The trough of the wave equals $I_0$ or the value of the homogeneously dissolved section as shown in FIG. 16. All residual parts of the wave other than the trough represent the inclusion of the inhomogeneous precipitant, and the height of the wave represents the content of the inhomogeneous precipitant. The content of the inhomogeneous precipitant can be determined using a calibration curve.

As set forth above, in minute measuring time analysis, the intensities based on the homogeneously dissolved section and the inhomogeneously precipitated section can be separated from each other, and the concentrations of the objective element in both sections can be obtained from the intensities.

Figure 17:
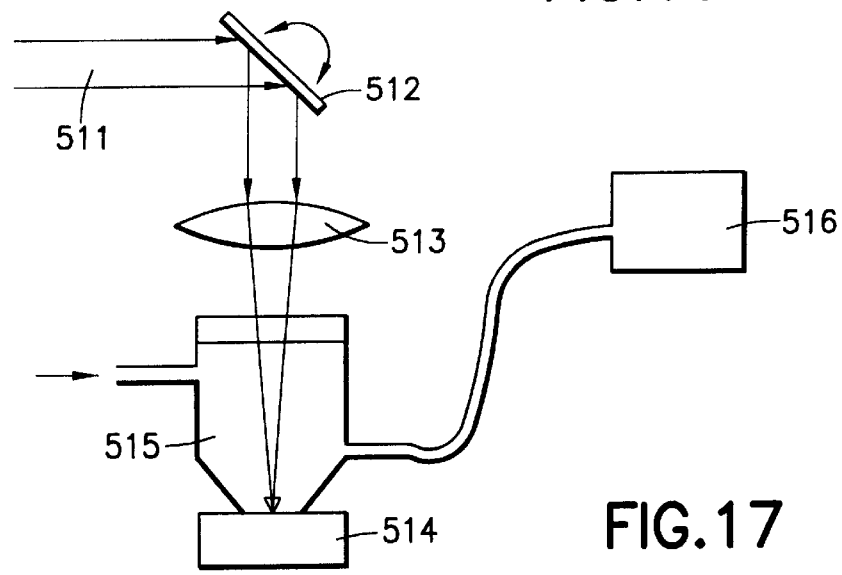
FIG. 17 is an outlined view of a laser vaporization apparatus for illustrating the movement of the position for analysis.

It is preferable that the frequency of the laser beam pulse be 50 Hz or more and the focused beam diameter range from 50 $\mu$m to 1 mm. The movement of the focal point is performed by parallel movement of the reflective mirror and the condenser lens. As shown in FIG. 17, the direction of the laser beam 511 is adjusted by the reflective mirror 512, and the laser beam 511 is converged onto the surface of the specimen 514 to be irradiated by the condenser lens 513. During irradiation, the analytical point is continuously varied by reciprocally rotating the reflective mirror 512 and synchronously moving the condenser lens 513.

The vaporized specimen is transferred from a probe 515, which comes in close contact with the specimen 514, to the inductively coupled plasma (ICP) spectrometer 516 as fine particles in an argon gas stream.

Figure 15:
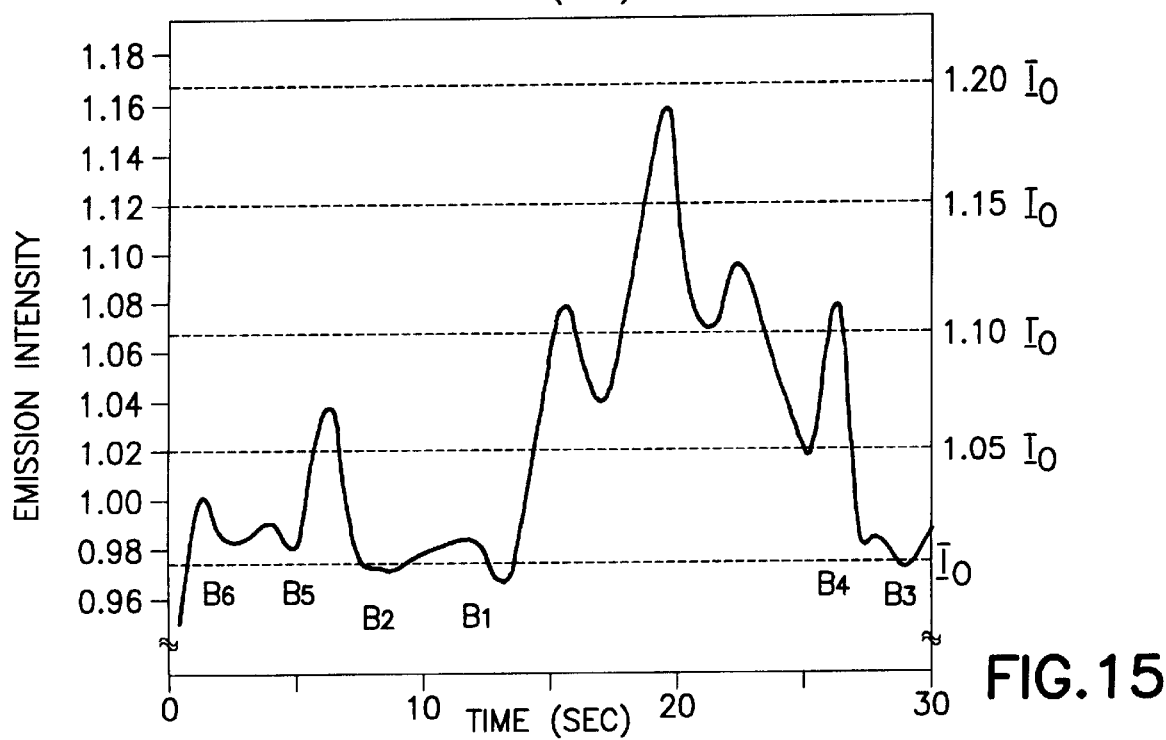
FIG. 15 is a graph illustrating the partition of the analytical region as an embodiment of waveform analysis.

FIG. 15 is a graph illustrating emission intensity of an objective element obtained with ICP spectrometry, in which each minute measuring time is set to be 100 msec. for a data acquisition time of 30 seconds. The graph having peaks and troughs consists of 300 momentary values each of which was obtained a minute measuring time of 0.1 secs.

An example of minute measuring time analysis is as follows: Select several troughs seriatim from the lowest trough, and calculate the median intensity and the average intensity $I_0$ of the several troughs. For example, six troughs $B_1$, $B_2$, - - - , $B_6$ are selected in FIG. 15. The concentration of the homogeneously dissolved section is determined from the average intensity $I_0$ using a calibration curve of intensity vs concentration. Next, the cumulative intensity is calculated from the total area of the regions having higher intensities than $I_0$, and is converted to the concentration of the inhomogeneously precipitated section using the calibration curve.

Examples of elements which are present in both the homogeneously dissolved state and the inhomogeneously precipitated state include calcium (Ca) in iron slag, carbon (C) in pig iron, and aluminum (Al), silicon (Si), manganese (Mn) and calcium (Ca) in steel. These elements can be separately determined in terms of individual states using this analytical procedure. Further, the cement components and sand components in mortar can be separately determined.

State analysis of Al in steel was carried out. Al in steel is present in a dissolved state in which Al is homogeneously dissolved in Fe and an oxide state in which Al forms acid-insoluble oxide and is inhomogeneously precipitated in the Fe matrix. Laser beam pulses with an output power of 10 W and a frequency of 1 kHz were generated and a beam diameter was converged to 100 $\mu$m. The analytical region had a depth of 20 Mm, a width of 2 mm and a length of 6 mm and the analytical point was varied at a moving rate of 0.2 mm/sec.

ICP spectrometry was carried out for each minute measuring time of 0.2 seconds for a data acquisition time of 60 seconds. The results were expressed as the relative emission intensity of Al to the main component Fe. The relative emission intensity to the main component is generally used to eliminate fluctuations in the results due to external disturbance.

Figure 14:
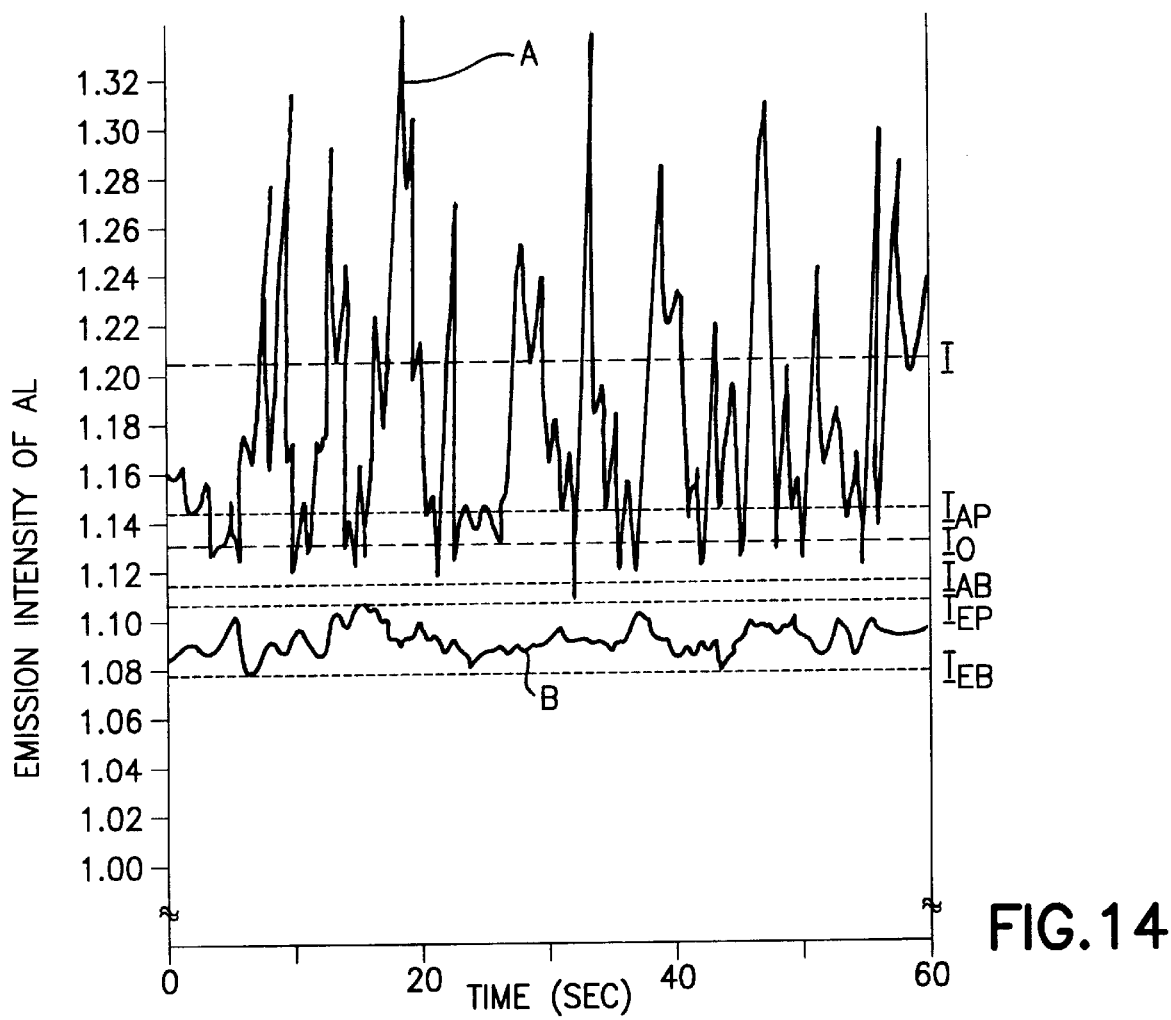
FIG. 14 is a graph illustrating an example of momentary values.

The results are shown in FIG. 14, wherein graph A represents an objective specimen and graph B represents a standard specimen not containing acid-insoluble Al. Graph B reflects the variation in data acquisition on acid-soluble Al homogeneously dissolved in the matrix and has a maximum intensity $I_{Ep}$ and a minimum intensity $I_{EB}$. On the other hand, the intensities in graph A include the intensity based on acid-insoluble Al, as well as the variation in data acquisition. That the variation in data acquisition is proportional to the acid-soluble Al content is assumed, the variation in data acquisition for acid-soluble Al in graph A is presumed in view of the variation for the standard specimen in graph B, and the intensity based on the acid-soluble Al is determined.

For example, it is assumed that the variation in data acquisition for acid-soluble Al in the objective specimen is $(I_{BP}-I_{BB})I_{AB}/I_{BB}$ wherein $I_{AB}$ represents the intensity of the lowest trough in graph A. The lower limit of the intensity corresponds to the lowest intensity $I_{AB}$, and the upper limit $I_{AP}$ is the sum of $I_{AB}$ and the variation set forth above. In other words, the observed intensity based on the acid-soluble Al ranges between $I_{AB}$ and $I_{AP}$. The average observed intensity $I_0$ represents the intensity based on the acid-soluble Al.

Next, the average intensity I is determined from intensities above $I_{AP}$. Because the average intensity I represent the intensity of the fine region including the acid-insoluble Al, the average intensity I include the intensity $I_i$ based on the acid-insoluble Al. Thus, the intensity $I_i$ based on the acid-insoluble Al is obtained by subtracting $I_0$ from I.

The products of $I_0$ and the cumulative minute measuring time, and Ii and the cumulative minute measuring time represents the respective cumulative intensities. These cumulative intensities are reduced to their respective concentrations using a calibration curve of intensity vs Al concentration. In FIG. 14, the acid-soluble Al concentration was 0.032 percent by weight and the acid-insoluble Al concentration was 0.003 percent by weight.

Application of Laser ICP Spectrometry to Converter Operation

Laser ICP spectrometry includes laser beam irradiation of the cut surface of a specimen, the transfer of the vaporized elements which are carried in a carrier gas to an ICP spectrometer, emission in induced plasma, spectrometry (wavelength and intensity) of the emitted light, and determination of elements.

The method is illustrated with reference to FIG. 18. A sample of approximately 30 mmφ by 70 mm was collected from a converter using a sublance. Sample 601 was cramped with cramps 619 and 620 at position A. The cramped sample 601 was immediately shifted to position B and cut with a cutter 603.

The cut sample was transferred to the laser irradiation position along rails 617 by a transfer means 616. The laser beam originated from a laser generator 605, was reflected with a reflective mirror 605, and converged with a condenser lens 610, was radiated onto the cut face of the sample 601 through the front end of a laser irradiation unit 607. The front end of the laser irradiation unit 607 came in close contact with the cut face of the sample 601, so as to collect vapor including various elements formed on the cut face of the sample 601. The vapor was transferred by argon gas or the like which was supplied from a gas generator 614 connected to the irradiation unit 607 via a pipe 613. The vapor in the carrier gas passed through a pipe 615 to reach an ICP spectrometer 606.

In this analytical apparatus, the cutting time of the sample was approximately 15 seconds, and the cut sample was immediately served for analysis without sample cooling, grinding or polishing of the sample surface. The analysis was completed in approximately 30 seconds. Thus, the neat analysis time was significantly reduced compared to conventional emission spectrometry (approximately 56 seconds). Further the total time for analysis can be significantly reduced since no preparation other than sample cutting and transfer is required. When this method is applied to a converter operation, the steelmaking time can be reduced, resulting in improved operation.

The converter operation using laser ICP spectrometry comprises the steps of:

(a) starting a blowing in a converter refining, setting a finish time of the blowing from a start time of the blowing in the converter refining;

(b) collecting a sample from the melt in the converter for a predetermined time period before the finish time of the blowing;

(c) mechanically cutting the collected sample to form a flat cross-section;

(d) determining the specified component of the cut face of the sample by laser ICP spectrometry; and (e) changing operation conditions based on the analytical results, or finishing the blowing operation without changing the operation condition and tapping immediately.

The analysis time of laser ICP spectrometry in accordance with the present invention is compared with that of conventional emission spectrometry in FIG. 19. The time required for sample collection with the probe attached to the chip of the sublance is approximately 12 seconds in both methods. The manual or mechanical transfer time of the sample to the analytical site is 22 seconds in both methods.

Figure 18:
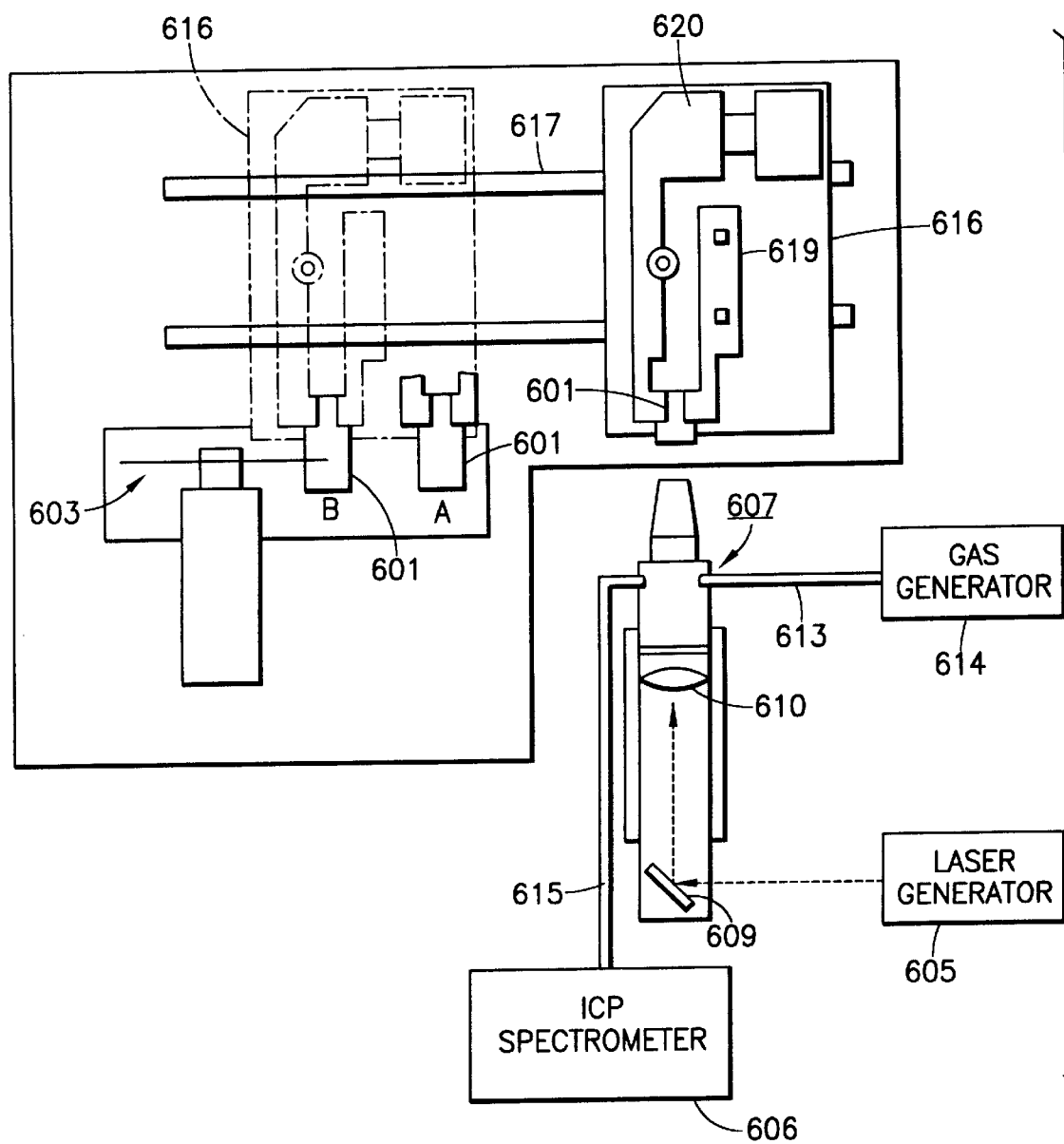
FIG. 18 is an outlined planar view of a laser ICP (inductively coupled plasma) analyzer.

In the present invention, the sample is cut using a unit as shown in FIG. 18 in a series of automatic procedures. The cutting time is 15 seconds in the present invention which is shorter than the 20 seconds in conventional emission spectrometry. The sample cooling and grinding steps can be omitted in the laser ICP spectrometry. In contrast, the sample manually installed in the spectrometer must be cooled with water and the analytical face must be cut to obtain a smooth surface. The cutting time requires 35 seconds. Thus, the preparatory time is shortened by approximately 60 seconds in laser ICP spectrometry. Further, the neat analysis time of approximately 30 seconds in laser ICP spectrometry is shorter than the approximately 56 seconds in emission spectrometry. As a result, the total analysis times from sample collection to completion of analysis are 79 seconds for laser ICP spectrometry and 170 seconds for emission spectrometry. Thus, laser ICP spectrometry can save approximately 91 seconds, resulting in improved efficiency of converter operation.

The converter operation process using laser ICP spectrometry in accordance with the present invention is compared with that using conventional emission spectrometry in FIG. 20. In the conventional process, the blowing time, for example, of 20 minutes, is previously determined before the start of the blowing. The sublance is inserted into the converter to collect the sample at 120 seconds before the finish time of the blowing, and the blowing is completed 120 seconds after the sublance insertion unless the process is changed.

Figure 20A:
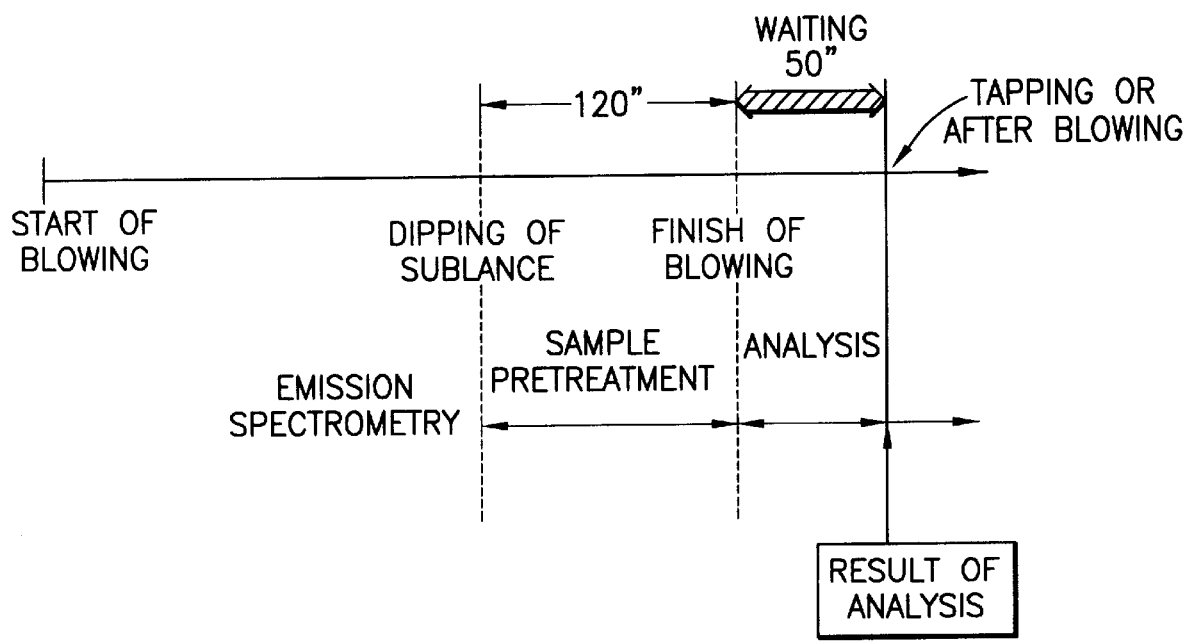
FIGS. 20A and 20B are diagrams in which the converter operation using a conventional emission spectrometry technique is compared with that in a laser ICP analysis method.

Since analytical results are obtainable after 170 seconds from the sublance insertion in conventional emission spectrometry, approximately 50 seconds after the finish of the blowing are spent as waiting time for tapping. Further, if the analytical results are out of the predetermined range, a blow-in procedure must be added after the waiting time-before the tapping. FIG. 20A illustrates the analytical step and the time period required for blowing in conventional emission spectrometry.

Figure 20B:
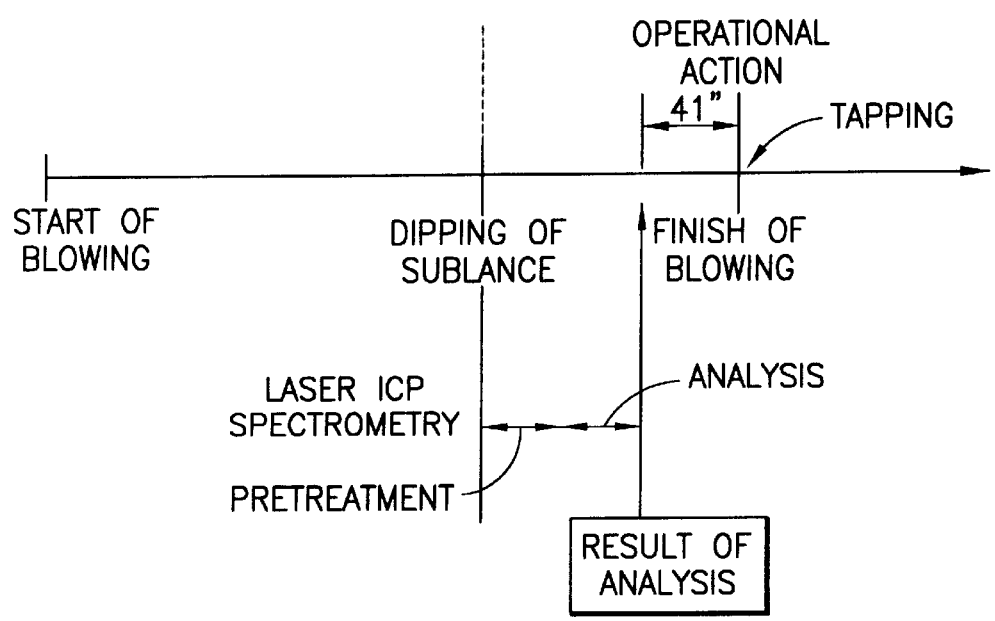

FIG. 20B illustrates the time period required for a typical converter operation using laser ICP spectrometry in accordance with the present invention. The sublance is inserted at 120 seconds before the scheduled finish of the blowing, and the time period from the start of sample collection to the completion of analysis is 79 seconds on average as set forth above. Thus, the analytical results are reported 41 seconds before the scheduled finish of the blowing. Therefore, the operation conditions can be changed in consideration to changes in finish time, if necessary, and the concentrations of objective elements at the end of the refining process, for example, the C, Mn and P contents of the molten steel, can be more accurately determined. Such changes in the operation conditions do not necessarily require an additional blowing process.

Consequently, laser ICP spectrometry in accordance with the present invention can save on waiting time for tapping, 50 seconds, and a blowing process may be added within the waiting timeaccording to demand. Tapping can be performed immediately after finish of the blowing.

When variations in the final components are not essential and confirmatory analysis is required, the sublance can be inserted 80 seconds before the scheduled finish of the blowing. Thus, the sublance may be inserted between approximately 80 and 120 seconds before the scheduled finish of blowing to collect the sample.

Elements to be analyzed include C, Mn, P and S in blow refining of carbon steel, and special components such as Cr, Ni, Mo, V, W, Nb and Ti in blow refining of stainless steel. These elements can be determined simultaneously. Other elements such as Si, Al, Sn, As and Pb can also be analyzed.

The operating process illustrated in FIG. 20 was performed using a 300-ton converter. Table 4 shows the results of a process in accordance with the present invention and a conventional process with a charge number of 150.

In the conventional process, the hitting ratios of final C and Mn contents were 90 and 85 percent respectively, the waiting time for tapping was 50 seconds on average, and 8 percent of charges required an additional blowing process because analytical values after the completion of blowing were out of the predetermined range.

In contrast, in the process in accordance with the present invention, analytical values were obtainable before the finish time of the blowing and operating conditions could be changed based on the analytical values. Thus, the hitting ratios of final C and Mn contents were 97 and 92 percent respectively, the waiting time for tapping was 5 minutes on average, and only 2 percent of charges required an additional blowing process.

As set forth above, the converter operation process using laser ICP spectrometry has the following advantages: an improved hitting rate; a short waiting time for tapping (one-tenth of the conventional process); and a decreased number of charges requiring additional blowing (2 percent). Further, 41 to 42 tapping cycles per 24 hours (a day) can be achieved in the process in accordance with the present invention, whereas 40 cycles can be achieved in the conventional process. Moreover, tapping temperature can be reduced due to the extremely short idle time, and durability of the converter refractory material is significantly improved.

TABLE 4

| Charge Number n = 150 | Hitting Final [C] | Rates of Contents [Mn] | Waiting Time for Tapping | Additional Blowing |
|---|---|---|---|---|
| Conventional | 90% | 85% | 50 sec. | 8% |
| This Invention | 97% | 92% | 5 sec. | 2% |

Application of Laser ICP Spectrometry to Quality Inspection of Cast Product in Continuous Casting Laser ICP spectrometry includes laser beam irradiation of the cut surface of a specimen, the transfer of the vaporized elements which are carried in a carrier gas to an ICP spectrometer, emission in induced plasma, spectrometry (wavelength and intensity) of the emitted light, and determination of elements.

Figure 21:
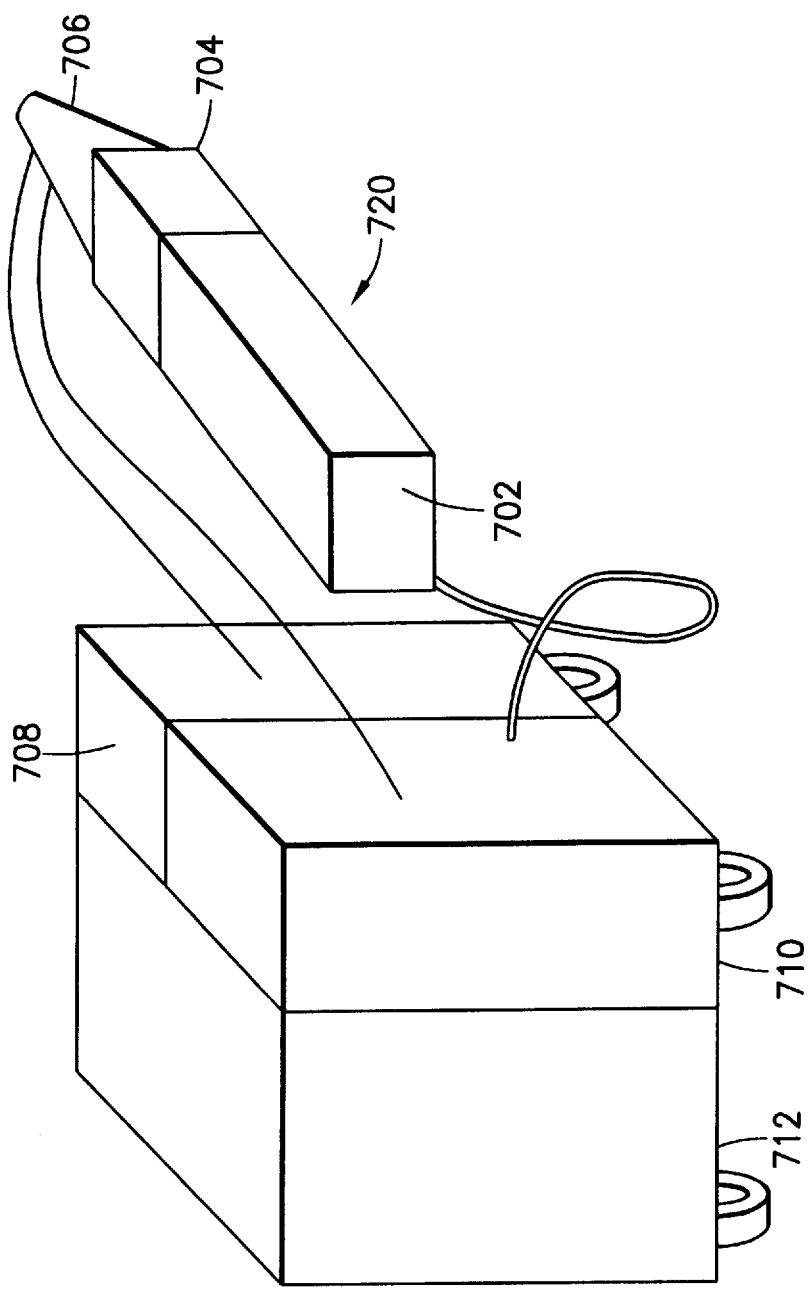
FIG. 21 is an outlined perspective view of a handy laser ICP spectrometer.

The method is illustrated with reference to FIG. 21. A movable analytical unit shown in FIG. 21 comprises a consolidation of a gas supply section 708, an ICP spectrometer 710 and a laser electrical power supply 712, and further comprises a laser irradiation unit 720.

A laser beam, which is generated from a laser oscillation section 702 by means of electrical power from the laser electrical power supply 712, is converged in an optical system 704 and radiated from a cell at the front end of the laser irradiation unit 720. The following are specifications of the unit:

Laser: YAG Q-switch laser Wavelength: 1.06 μm
Average output power: 10 W
Frequency of Q-switch: 1 KHz
Pulse width: 100 nsec.
Condenser lens: F=100 mm
Minimum irradiation area: 2 μm square
Grinding of Analytical Surface: After belt grinding, laser grinding 150 sec.

In this analytical unit, C, Mn, Si, P, S, Cr and the like require approximately 30 seconds of analysis time. The accuracy does not depend on the temperature of the analytical surface, unlike conventional emission spectrometry. After a sequentially cast product is cut according to a given schedule, the cut product is inspected whether the cutting is ordinary or not. Therefore, the cross-sectional surface of the top or last cast product of the preceding charge and the cross-sectional surface of the bottom or first cast product of the following charge are analyzed in a hot state to inspect whether the cutting is ordinary or not, and the cast product is subjected to recutting if necessary.

The procedure of quality inspection of the cast product in sequence casting comprises the steps of:

(a) cutting the cast product produced by sequence casting at the front and the rear of the transition area according to a given schedule;

(b) determining predetermined elements in the central cross-section of the cut cast product from the preceding charge by laser ICP spectrometry;

(c) determining predetermined elements in the peripheral cross-section of the cut cast product from the following charge by laser ICP spectrometry; and (d) inspecting the quality of the cast products based on these results.

In the present invention, melted metals include steel, aluminum, copper, and alloys thereof, because laser ICP spectrometry is capable of analysis of all kinds of metals.

Figure 22:
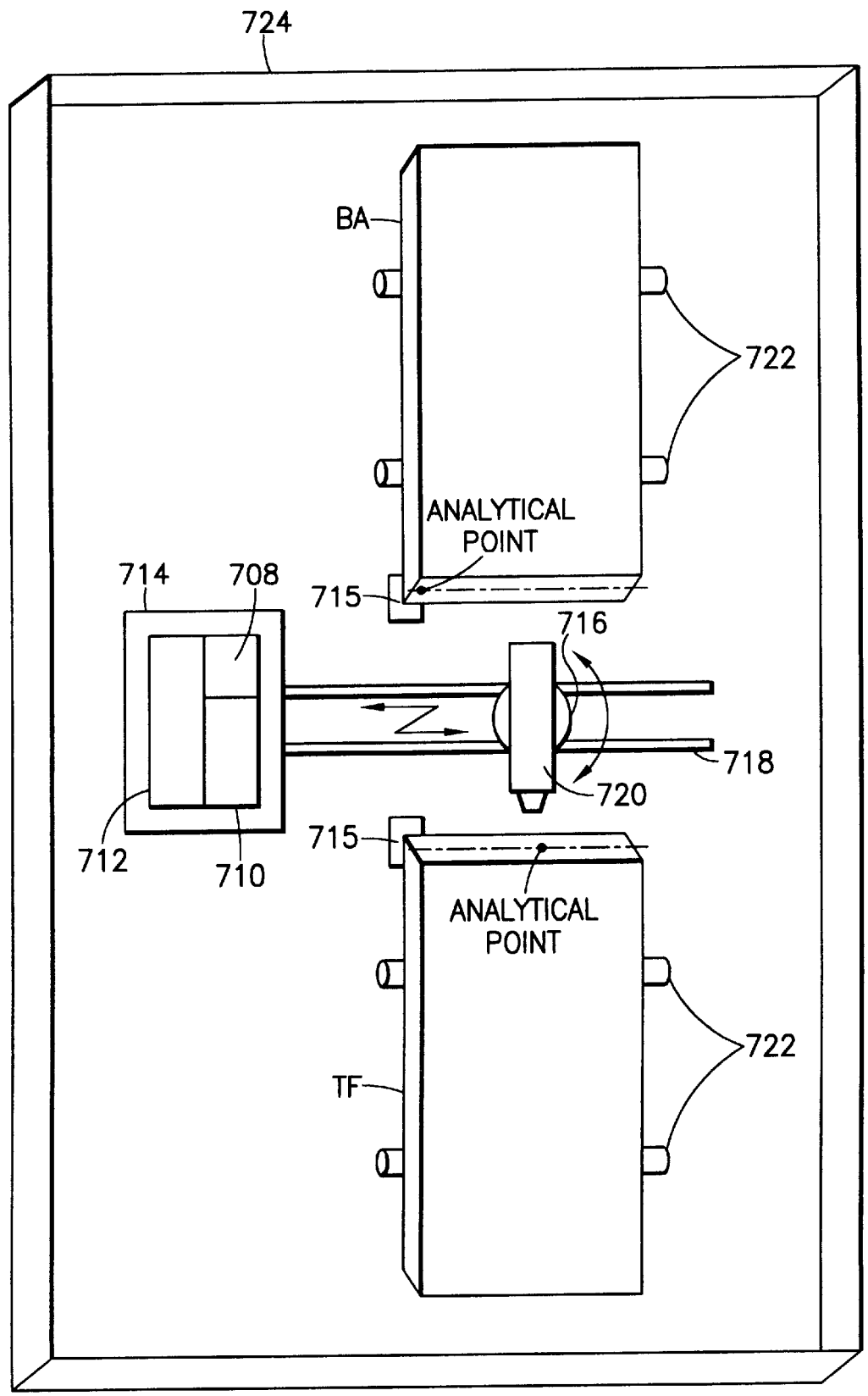
FIG. 22 is a planar view illustrating an embodiment for performing the present invention.

An embodiment in accordance with the present invention will now be illustrated with reference to FIG. 22. After a sequentially cast product is cut according to a given schedule, the bottom cast product (BA) of the following charge and the top cast product (TF) of the preceding charge are transferred to an analytical stand 724. The analytical stand 724 is placed in the continuous casting plant and is connected to a roll stand for conveying the cast products. The BA and TF cast products set forth above are transferred to the predetermined positions, respectively, in the analytical stand 724, in response to their respective positioning sensors 715.

The laser irradiation unit 720 of the ICP spectrometer which is placed in a laser chamber 714 is moved along rails 718 to the midpoint between both cast products. As set forth above, the central cross-sectional surface is analyzed for the top cast product of the preceding charge, while the laser irradiation unit 720 moves to the cast product and comes in contact with the point to be analyzed. Analysis time required is approximately 30 seconds.

Next, the laser irradiation unit 720 is rotated on a turn table 716 to analyze the peripheral cross-sectional surface of the bottom cast product of the following charge. Analysis time required is also approximately 30 seconds. During analysis, these cast products are in a red-heating state, because these are transferred immediately after the seam is cut off.

As set forth above, the cross section of the cast product in a red-heating state can be analyzed by laser ICP spectrometry. Thus, the continuous casting metal can be cut with an on-line cutter and the cut cast products are immediately transferred to the analytical stand to be analyzed in a hot-heating state. Since positioning and analysis are promptly performed, the analysis time including the positioning time is approximately 2 minutes. Thus, the total analysis time including transfer and positioning of the cast product is within 10 minutes, whereas conventional methods require four to five days.

Thus, the cast product can be transferred to the next rolling step if the analytical results are within predetermined ranges (so called direct transfer rolling). If the analytical results deviate from the predetermined ranges, the cast product is transferred to a recutting section, recut there, transferred to the analytical stand, and analyzed again.

A plurality of points to be analyzed may be selected if necessary. The analysis time required for one point is within 2 minutes, including positioning time.

Elements to be determined include C, Mn, P, S, Si, and Al for the cast product of carbon steel. Further, Cr, Ni, Mo, V, W, Nb and the like are determined for the cast product containing particular components, according to demand. The present invention is applicable to not only sequence casting of molten steel, but also sequence casting of aluminum, copper, and alloys thereof.

Application of Laser ICP Spectrometry to Check of Central Segregation of Cast Product in Continuous Casting A rapid inspection procedure of central segregation of cast product in continuous casting comprises the steps of:

(a) cutting the continuously cast product according to a predetermined schedule;

(b) determining predetermined elements in at least one cut product by laser ICP spectrometry, in which each cut product is analyzed at the center or along a line including the center on the cut surface; and (c) checking the central segregation of the cast product based on the analytical results.

An embodiment in accordance with the present invention will now be illustrated with reference to FIG. 23. The cast product such as slab produced by continuous casting is cut to the cast product 711 according to a predetermined schedule and transferred to an analytical stand 724. The analytical stand 724 is placed in the continuous casting plant and is connected to a roll stand for transferring the cast product. The cast product 711 is transferred to a given position in the analytical stand 724. The position of the cast product 711 is determined by a positioning sensor 715.

A laser irradiation unit 720 of an ICP spectrometer is moved from a laser chamber 714 to almost the center of the cast product 711 along the rails 718. The laser irradiation unit 720 moves to the analytical point on the cut face of the cast product 711 so that the front end of the laser irradiation unit 720 comes in contact with the cut face. The laser irradiation unit 720 is scanned within approximately 3 mm in the vertical direction from the center line for central segregation analysis. Analysis is performed by continuous scanning in which the laser irradiation unit 720 crosses the center line, or by stepwise scanning in which the unit 720 crosses the center line and stops at a given interval, for example 0.5 mm. Central segregation can be surely analyzed by scanning ranging vertical 3 mm, since the central segregation generally has a width or thickness of 1 mm or less in the slab. Thus, analysis is performed by vertical movement of the laser beam without the movement of the laser irradiation unit 720, for approximately 60 seconds. in the stepwise scanning, the laser irradiation unit 720 is stepwise moved.

After completing analysis, the laser irradiation unit 720 may move along the rails 718 to analyze other positions, if necessary. This procedure also requires approximately 60 seconds of analysis time. The cast product is still in a hot-heating state because it is transferred immediately after cutting.

Figure 23:
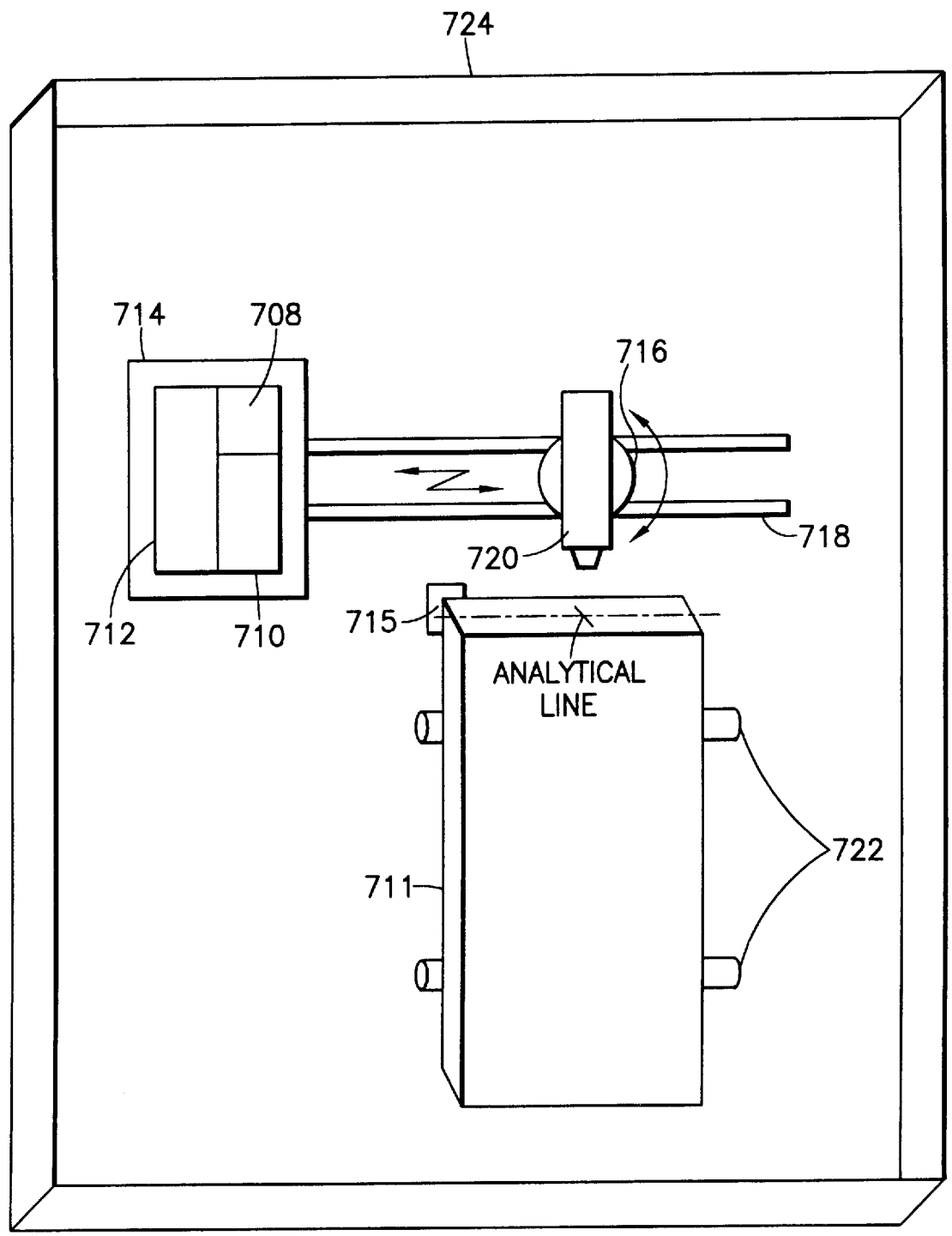
FIG. 23 is a planar view illustrating another embodiment for performing the present invention.

Although FIG. 23 illustrates a slab as an example of the cast products, other cast products such as square billet and round billet can also be analyzed in a similar manner. In square and round billets, the central segregation has a dot shape, not a line shape.

As set forth above, the cross section of the cast product in a red-heating state can be analyzed by laser ICP spectrometry. Thus, the continuous casting product can be cut with an on-line cutter and the cut cast product is immediately transferred to the analytical stand to be analyzed in a hot-heating state. The analysis time is approximately 2 to 5 minutes. Thus, the total analysis time including transfer and positioning of the cast product is within 10 minutes, whereas conventional methods require four to five days.

Thus, the cast product can be transferred to the next rolling step if the analytical results are within predetermined ranges (so called direct transfer rolling). If the analytical results deviate from the predetermined ranges, the usage (for example, customer or type) of the cast product is changed or ceased.

A plurality of points to be analyzed may be selected if necessary. The analysis time required for one point ranges from 2 to 5 minutes, and total time including positioning time is within 10 minutes.

Elements to be determined include C, Mn, P, S, Si, and Al for the cast product of carbon steel. Further, Cr, Ni, Mo, V, W, Nb and the like are determined for the cast product containing particular components, according to demand. In copper alloys and aluminum alloys, elements composing alloys can be determined.

Figure 3A:
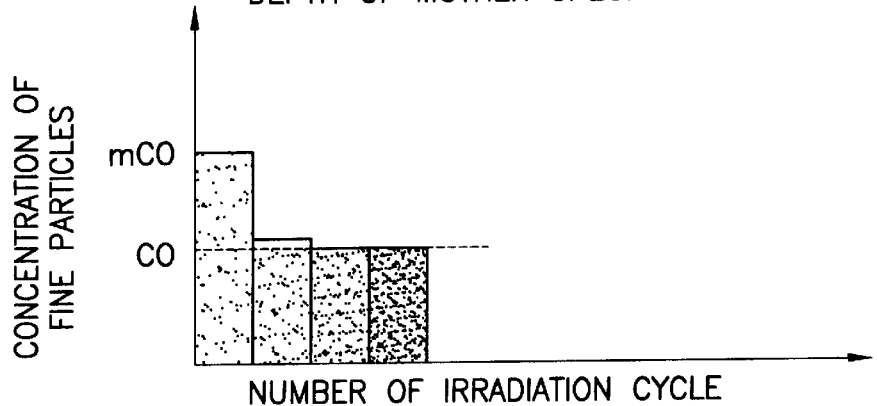
FIGS. 3A and 3B are graphs illustrating the correlations between irradiation cycle number and the concentration of fine particles, and between the depth and the concentration of the mother specimen, when the selective vaporization ratio m is more than 1.
Figure 3B:
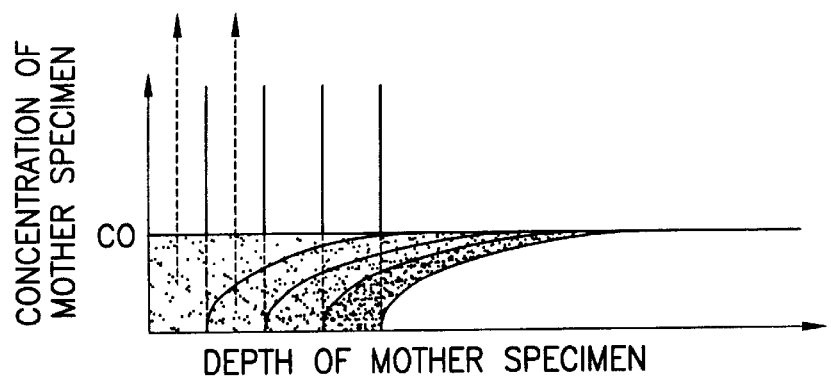
Figure 24A:
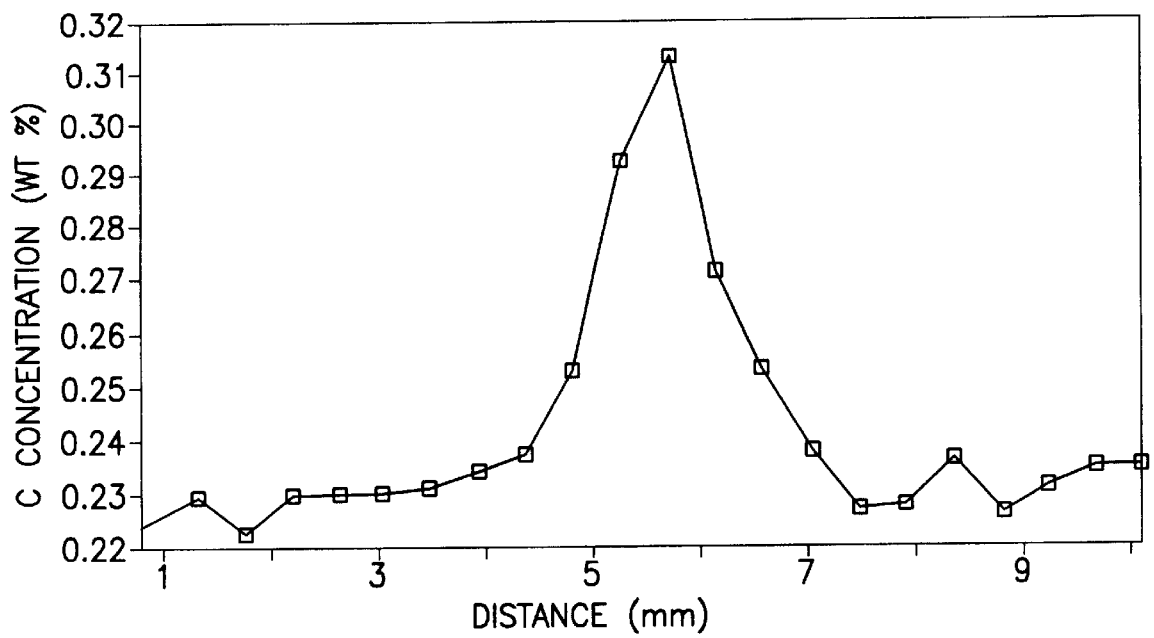
FIGS. 24A, 24B and 24C are graphs illustrating the results of spot analysis of the central segregation of continuously-cast carbon steel.
Figure 24B:
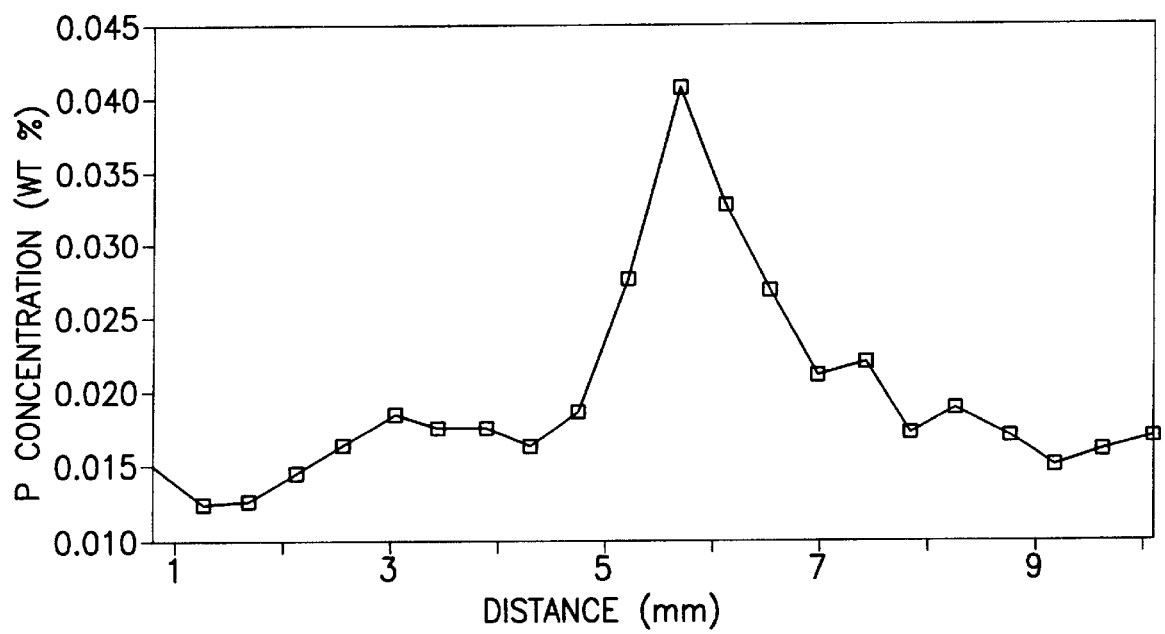
Figure 24C:
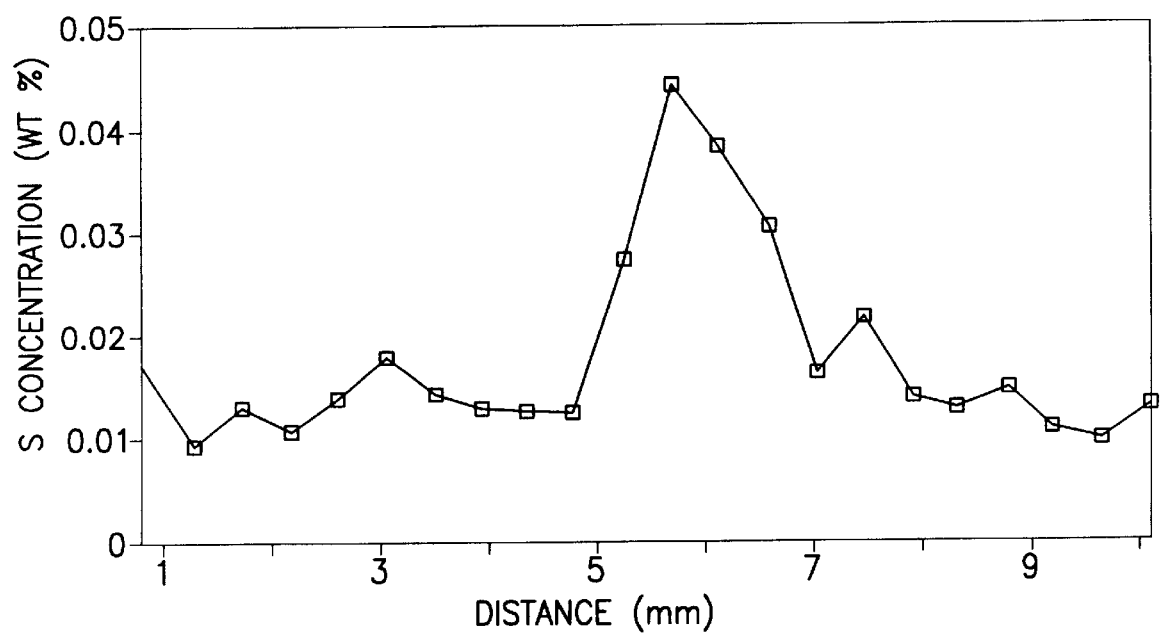

As an example, analytical results of the central segregation on the cut face of a slab produced continuous casting of carbon steel containing 0.23 percent by weight of carbon are shown in FIG. 24. The central segregation was located at about 6 mm of the horizontal axis. The concentrations of C, P and S were determined stepwise at an interval of 0.5 mm. It was concluded that this slab exhibited high central segregation as shown in FIG. 3 and was unsuitable for the objective usage. Thus, the usage of the slab was changed.

Application of Laser ICP Spectrometry to Check of Central Segregation of Cast Ingot A rapid inspection procedure of central segregation of a cast ingot comprises the steps of:

(a) cutting out the top and bottom of a rough-rolled cast ingot according to a predetermined schedule;

(b) analyzing the cut faces of the top and bottom of the cast ingot by laser ICP spectrometry; and (c) checking the central segregation of the cast ingot based on the analytical results.

An embodiment in accordance with the present invention will now be illustrated with reference to FIG. 25. The cast ingot produced by casting or rough rolling is cut according to a predetermined schedule and the cut top and bottom are transferred to an analytical stand 724. The analytical stand 724 is placed in the casting plant and is connected to a roll stand for transferring the cast ingot. The cut cast ingot 701 is transferred to a given position in the analytical stand 724. The position of the cast ingot 701 is determined by a positioning sensor 715.

A laser irradiation unit 720 of an ICP spectrometer is moved from a laser chamber 714 to almost the center of the cast ingot 701 along the rails 718. The laser irradiation unit 720 moves to the analytical point on the cut face of the cast ingot 701 so that the front end of the laser irradiation unit 720 comes in contact with the cut face. The laser irradiation unit 720 is scanned within approximately 3 mm in the vertical direction from the center line for central segregation analysis. Analysis is performed by continuous scanning in which the laser irradiation unit 720 crosses the center line, or by stepwise scanning in which the unit 720 crosses the center line and stops at a given interval, for example 0.5 mm.

When the cast ingot is a rough-rolled slab, central segregation can be surely analyzed by scanning ranging vertical 3 mm, since the central segregation generally has a width or thickness of 1 mm or less inn the slab. Thus, analysis is performed by vertical movement of the laser beam without the movement of the laser irradiation unit 720, for approximately 60 seconds. in the stepwise scanning, the laser irradiation unit 720 is stepwise moved.

After completing analysis, the laser irradiation unit 720 may move along the rails 718 to analyze other positions, if necessary. This procedure also requires approximately 60 seconds of analysis time. The cast ingot is still in a hot-heating state because it is transferred immediately after cutting.

Figure 25:
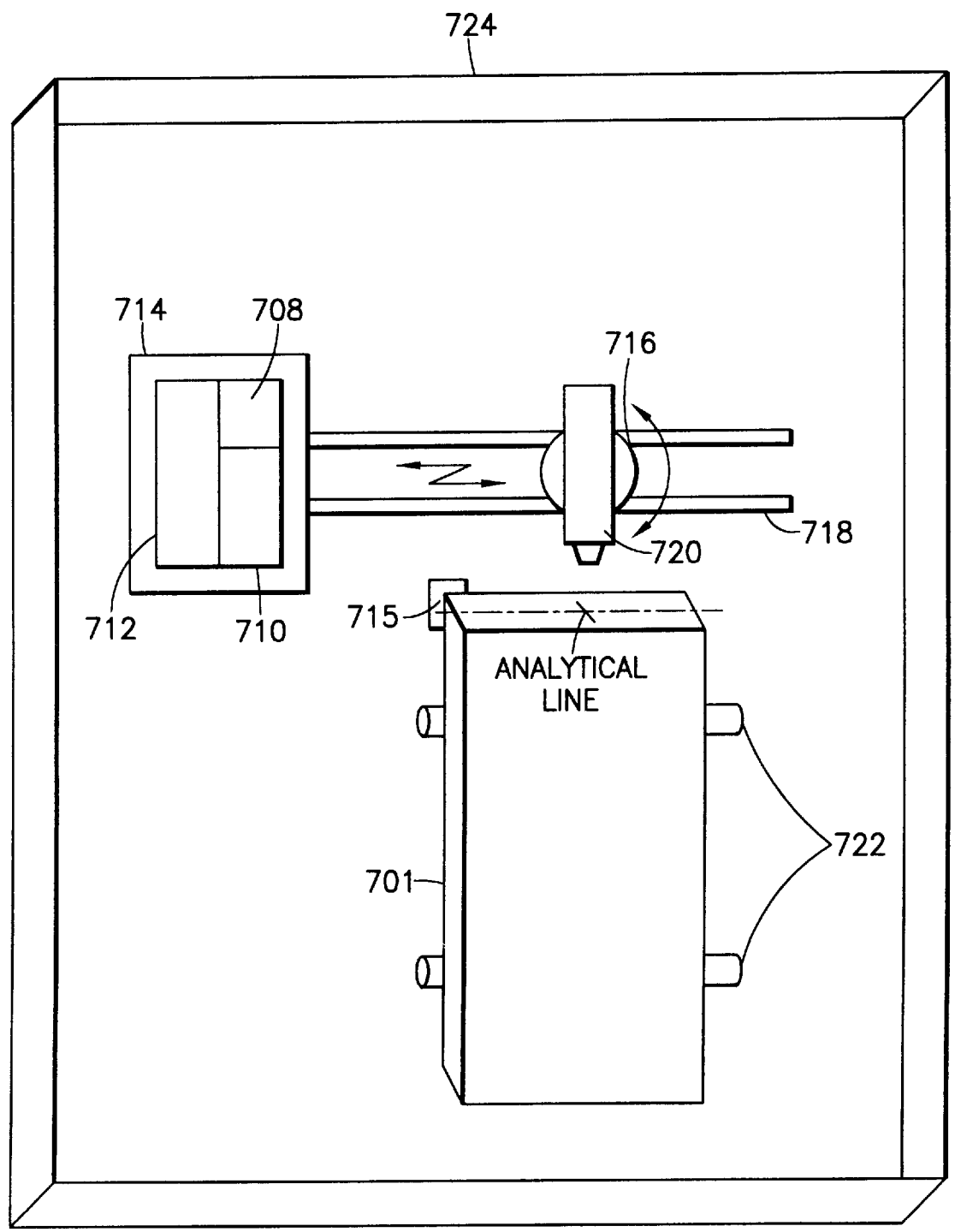
FIG. 25 is a planar view illustrating an embodiment of the analysis of the central segregation of rough-rolled material using a handy laser ICP spectrometer.

Although FIG. 25 illustrates a rough-rolled slab as an example of the cast ingot, other cast ingots such as square bloom and round bloom can also be analyzed in a similar manner. In square and round blooms, the central segregation has a dot shape, not a line shape.

As set forth above, the cross section of the cast ingot in a red-heating state can be analyzed by laser ICP spectrometry. Thus, the cast ingot can be cut with an on-line cutter and the cut cast ingot is immediately transferred to the analytical stand to be analyzed in a hot-heating state. The analysis time is approximately 2 to 5 minutes. Thus, the total analysis time including transfer and positioning of the cast ingot is within 30 minutes, whereas conventional methods require four to eight days.

Thus, the cast ingot can be transferred to the next rolling step if the analytical results are within predetermined ranges (so called direct transfer rolling). If the analytical results deviate from the predetermined ranges, the cast ingot is transferred to a recutting section, recut there, transferred to the analytical stand, and analyzed again.

A plurality of points to be analyzed may be selected if necessary. The analysis time required for one point ranges from 2 to 5 minutes, and total time including positioning time is within 10 minutes.

Elements to be determined include C, Mn, P, S, Si, and Al for the cast ingot of carbon steel. Further, Cr, Ni, Mo, V, W, Nb and the like are determined for the cast ingot containing particular components, according to demand. In copper alloys and aluminum alloys, elements composing alloys can be determined.

Apparatus Used for Analysis of Metals

Analysis of the metal is performed by using a system having a carriage which carries a laser oscillator, a laser beam controller, a laser irradiation cell and so forth. The carriage is moved to a position where it opposes the metal to be analyzed and, with the laser beam irradiating port of the cell held in contact with the analytical surface of the metal, and the laser is activated to emit a laser beam which irradiates the analytical surface of the metal, so that fine particles are freed from the analytical surface of the metal. The fine particles are then conveyed to an analyzer such as a spectrometer by means of an inert carrier gas such as an argon gas.

It is therefore possible to directly, quickly and properly analyze the metal to determine the components of the metal, regardless of the metal temperature and without requiring troublesome work for cutting the metal into a specimen of specific shape and size adapting to the spectrometer.

Figure 26:
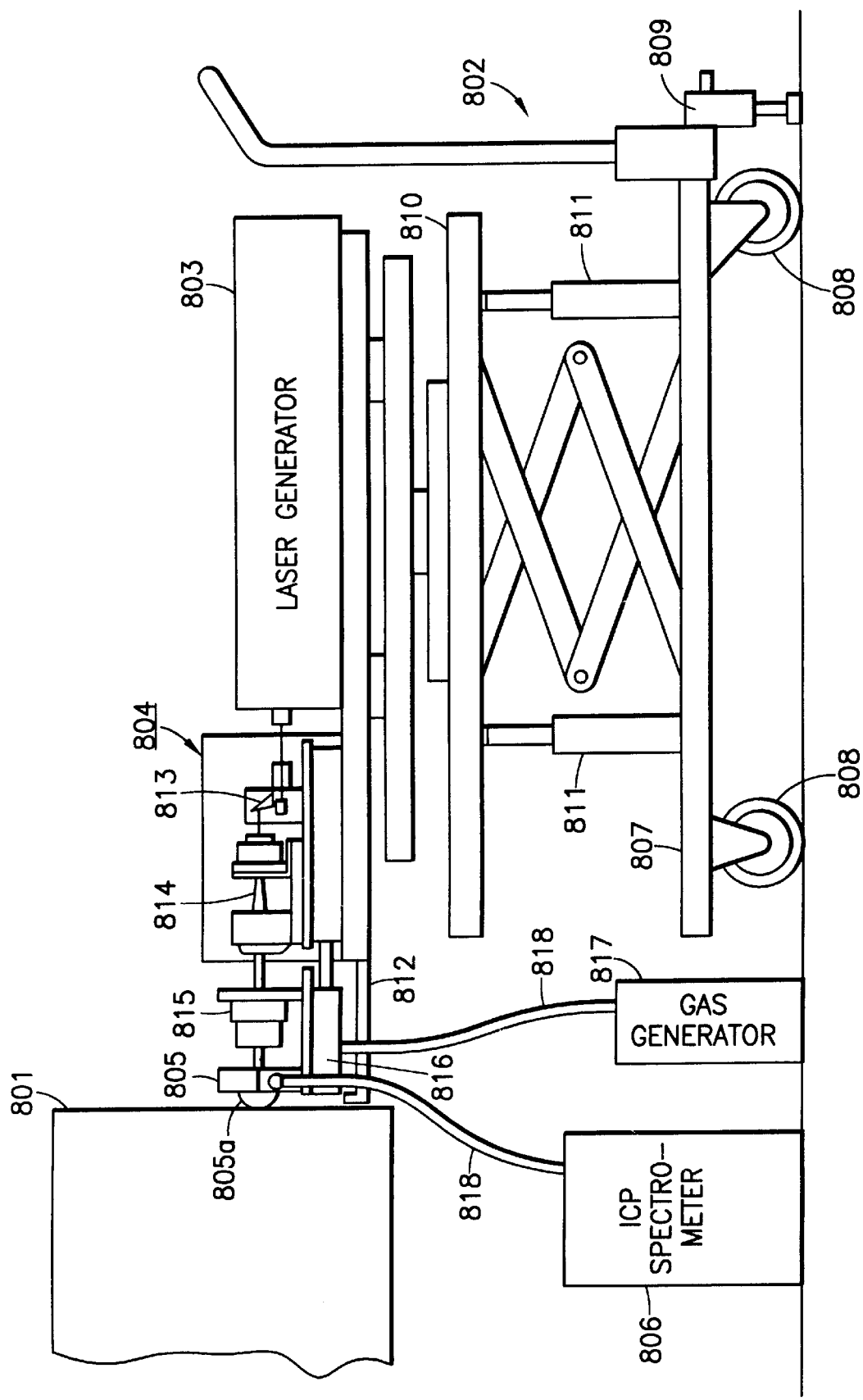
FIG. 26 is an outlined front view illustrating an embodiment of an apparatus in accordance with the present invention.

FIG. 26 is a schematic front elevational view of the apparatus in accordance with the present invention. As will be seen from this Figure, the apparatus has a carriage 802 which is movable towards the metal to be analyzed, e.g., a billet 801. The carriage 802 carries a laser oscillator 803, a laser beam controller 804 which performs focal control of the laser beam from the laser oscillator 803, and a laser beam irradiating cell 805.

The carriage 802 has a base 807 which is provided at its underside with wheels 808 and equipped with a stopper-809. The carriage 802 further has a liftable table 810 which is moved up and down by a lifting gear 811 such as a hydraulic cylinder. The above-mentioned laser oscillator 803, laser beam controller 804 and the laser beam irradiating cell 805 are mounted on the table 810. The table 810 also carries a plurality of positioning arms 812 which are adapted to abut the analytical surface of the metallic specimen 801 so as to properly position the whole apparatus. These positioning arms 812, each having an L-shaped end, are extended horizontally from an end of the table 810 in parallel with one another.

The laser oscillator 803 is operative to focus the laser beam at a point on the analytical surface of the billet 801 so that the energy of the beam is applied at a large density to evaporate part of the billet 801, thereby releasing fine particles.

The laser beam controller 804 includes a laser beam reflective mirror 813, a beam expander 814 for improving coherence of the laser beam and a condenser lens 815. The lens 815 is provided on a base 816 which also is carried by the table 810 so as to be moved horizontally by the action of a pneumatic cylinder. The leaser beam irradiating cell 805, having the laser beam irradiating port 805a for contact with the analytical surface of the billet 801, is provided on an end of the base 816. The reflective mirror 813 and the condenser lens 815 are rotatable and shiftable so as to enable change of the optical axis, as well as control of the coverage of the laser beam on the analytical surface of the billet 801. Thus, the laser beam controller 804 is effective in attaining higher rate of generation of fine particles from the billet 801, as well as higher accuracy of the analysis, while suppressing any tendency of analysis failure attributable to segregation analysis.

The arrangement may be such that the laser source is not carried by the carriage 802 and the laser beam from the laser source is guided through an optical fiber. It is, however, necessary that the laser beam of high power emitted from the laser source after turning on of the Q switch is guided to the same position as the laser beam controller 804. To this end, it is essential that the high-power laser output portion is disposed on the carriage 802 together with the laser beam controller 804.

As stated before, the laser beam irradiating cell 805 and the condenser lens 815 are mounted on the table 816 which is movable horizontally. It is therefore possible to press the cell 805 against the analytical surface of the billet 801 so as to bring the laser beam irradiation port 805a on the end of the cell 805 into close contact with the analytical surface, by activating the pneumatic cylinder to urge the base 816. It is necessary to previously adjust the focal length of the condenser lens 815 such that the laser beam is focused on the analytical surface when the cell 805 is pressed against the analytical surface of the billet 801. The condenser lens 815 may be adjustably disposed on the table 810 together with the laser beam controller 804.

Presence of any gap between the irradiating port 805a of the laser beam irradiating cell 805 and the analytical surface of the billet 801, which may undesirably occur when the irradiating port 805a is pressed against the analytical surface, causes a reduction in the rate of transportation of the fine particles which are generated from the billet as a result of irradiation with the laser beam, with the result that the accuracy of the analysis to be performed by the analyzer is impaired. It is therefore critical that the irradiation port 805a of the cell 805 is kept in contact with the analytical surface of the billet 801 as closely as possible.

In the described embodiment of the invention, therefore, when the laser irradiating port 805a on the end of the cell 805 is pressed against the analytical surface of the billet 801 by the action of the pneumatic cylinder 816, the ends of the positioning arms 812 which project horizontally from an end of the table 810 are caused to abut the analytical surface of the billet 801, thus achieving high degree of closeness of contact between the irradiating port 805a and the analytical surface of the billet 801.

More specifically, the end extremities of the L-shaped ends of the positioning arms 812 are formed to extend in parallel with the plane of the laser beam irradiating port 805a of the cell 805, so that any relative inclination or twist between the analytical surface and the surface of the cell 805 can be detected when the positioning arms 812 are brought into contact with the analytical surface of the billet 801. It is therefore possible to set the apparatus such that the laser beam irradiating port 805a of the cell 805 is held in close contact with the analytical surface of the billet 801.

Further improvement in the analytical accuracy can be achieved by using a monitor system which monitors the state of contact between the laser beam irradiating port 805a of the cell 805 and the analytical surface of the billet 801 so as to confirm safe contact, each time the billet is changed.

A quartz glass window is provided in the end of the cell 805 opposite to the end in which the laser beam irradiation port 805a is provided. An inert gas source 817 and an RF ICP (Inductively Coupled Plasma) spectrometer 806 are connected through flexible conduits 818 to the interior of the cell 805. The inert gas source 817 supplies an inert gas such as argon into the cell 805 so as to convey and transport the fine particles generated from the billet 801 as a result of irradiation with the laser beam. The fine particles conveyed by the inert gas is introduced into the ICP spectrometer so as to be subjected to analysis for determination of the composition of the fine particles.

It is necessary that the analytical surface of the billet 801 is beforehand ground to get rid of any matter such as an oxide film. The grinding can conveniently be performed by a small-sized disk grinder or a belt grinder. Such a grinding device may be mounted on the carriage 802 together with the laser beam controller 804 or may be provided separately from the carriage 802.

The apparatus of the present invention following the specifications shown below was subjected to an analysis of composition of hot billets.

Cell: A cell made of SUS was used. A bellows spring was incorporated in the contact portion of the cell in order to absorb any deviation of contact angle between the cell and the specimen.

Laser: An Nd-YAG laser (wavelength 1.06 $\mu$m) with supersonic Q switch was used.

Analyzer: ICP spectrometer was used as the analyzer

The carriage 802 was moved to a position where it faces the analytical surface of the billet 801. A belt grinder having a grinding belt with #60 zirconia grains was installed on the carriage 802 in parallel with the laser beam controller 804 and the laser beam irradiation cell 805, so as to serve as the grinding device. Convexities of 2 to 3 mm high, originally presented on the surface of the billet of 30 mm wide and 30 mm long, were removed so that the analytical surface of the billet was smoothed by the grinding in about 10 seconds. Transfer os heat from the billet to the grinding belt during the grinding was negligibly small. It was also confirmed that the analytical surface of the billet could be smoothed in about 10 seconds also by the use of a zirconia-grain disk grinder of 150 mm diameter.

After the grinding of the analytical surface of the billet 801, the irradiating port 805a of the laser beam irradiating cell 805 was brought into close contact with the ground surface of the billet 801, by the combined effect of the movement of the carriage 802, vertical adjustment of the table 810 and the horizontal adjustment of the table 816, with the assist of the positioning arms 812. In order to confirm the tightness of the seal formed between the laser beam irradiating port 805a of the cell 805 and the analytical surface of the billet 801, monitoring was conducted by using a flowmeter or an argon intensitometer.

Then, the laser oscillator 805 was excited to emit a pulsating laser beam of 1 KHz so as to irradiate the analytical surface of the billet 801 at an average power of 12 W. Consequently, the steel material on the analytical surface was evaporated to release fine particles which were then transported to the ICP spectrometer 806 by means of argon carrier gas blown into the cell 805 from the gas source 817.

The ICP spectrometer 806 was operated with 1.5 KW power at 27.12 MHz, while the flow rates of the plasma gas, auxiliary gas and the carrier gas were respectively maintained at 15 liter/min, 1 liter/min and 1 liter/min, so that the fine particles generated as a result of the evaporation of the specimen were directly excited to illuminate to enable determination of the composition by the spectrometer. Consequently, the composition of the billet 801 could be analyzed to determine the constituents properly and quickly in a time which was as short as about 60 seconds.

According to the present invention, the specimen picked up from the furnace and then solidified is adapted to be moved between the specimen cutting device and the laser analyzing system, by means of a specimen moving apparatus. In operation, therefore, the specimen is cut by the cutting device so as to expose the analytical surface, and the specimen with the exposed analytical surface is conveyed immediately after the cutting to the position where the laser analyzing system is situated, so that the laser beam can be applied without delay. Consequently, matters such as oxide film on the specimen surface are removed by the laser beam, and fine particles are released from the specimen as a result of the irradiation with the laser beam are transported by the inert carrier gas to the analyzer which analyzes the chemical composition of the specimen. It is therefore possible to quickly and properly analyze the specimen composition even when the specimen is still red-heated.

Figure 27:
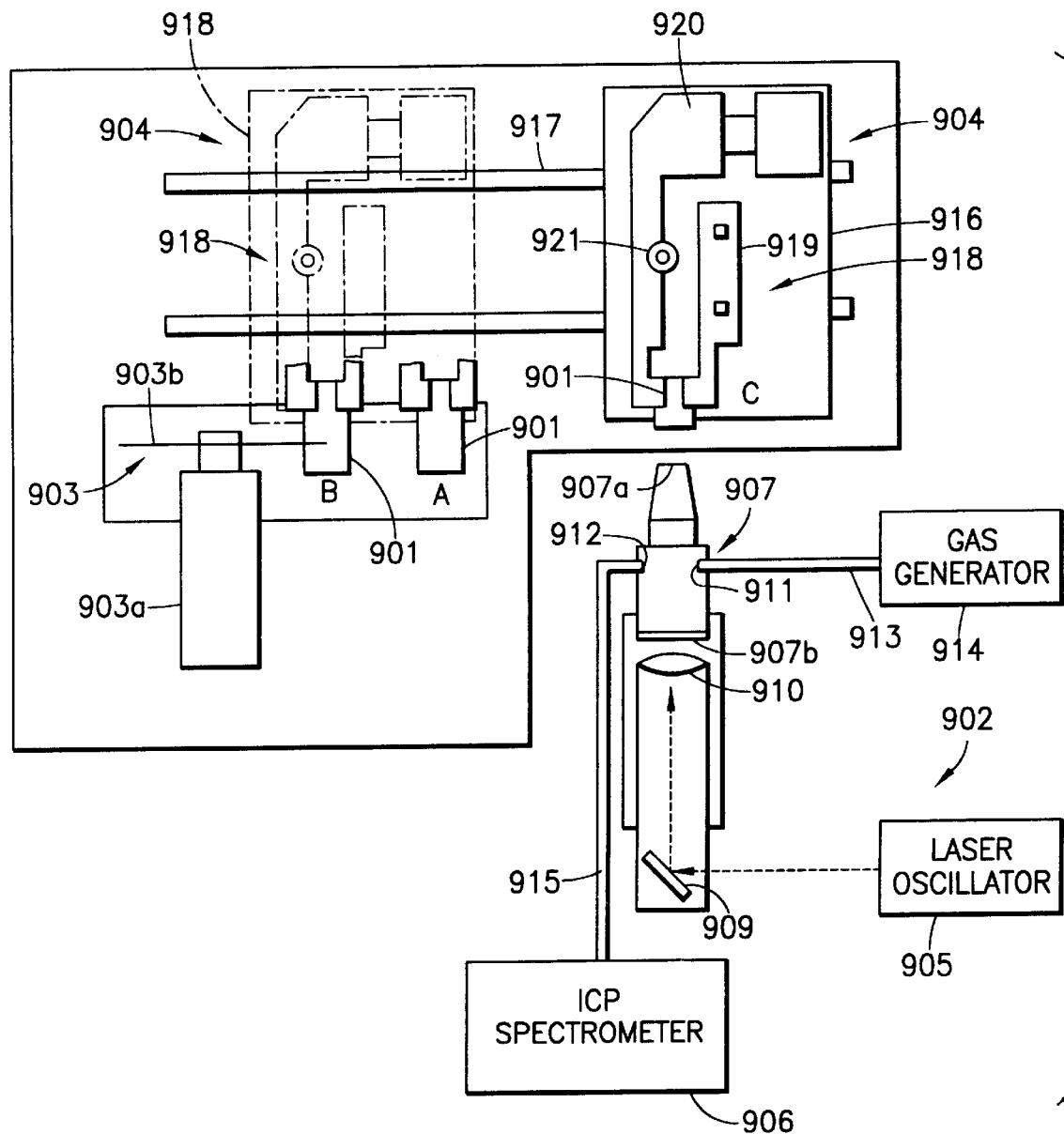
FIG. 27 is an outlined planar view illustrating another embodiment of the apparatus in accordance with the present invention.

A description will now be given of an apparatus in accordance with the present invention, while making reference to the accompanying drawings. FIG. 27 is a schematic plan view of the apparatus embodying the present invention. As will be seen from this Figure, the apparatus has a laser analyzer 902 for irradiating the specimen with a laser beam so as to analyze the chemical composition to determine the constituents of the composition, a specimen cutting device 903 for cutting the specimen 901 to expose the analytical surface to be examined, and a specimen chucking conveyor device 904 which is movable between the specimen cutting device 903 and the laser analyzer 902 so as to set the specimen sequentially at positions for cutting by the specimen cutting device 903 and analysis by the laser analyzer 902.

The laser analyzer 902 includes a laser oscillator 905 for irradiating the specimen 901 with a laser beam so as to generate fine particles of the material of the specimen 901, an ICP spectrometer 906, a laser irradiating cell 907 which is provided in its one end with a closable laser irradiating port 907a and at its other end with a quartz glass window 907b, a laser guide tube 908 having a laser beam reflective mirror 909 and a condenser lens 910 incorporated therein, and a gas source 914 which supplies a carrier inert gas such as argon into the cell 907 so as to convey the fine particles generated as a result of irradiation of the specimen 901 with the laser beam.

The cell 907 is provided at its one side with a gas inlet port 911 and at its other side with a gas outlet port 912. The above-mentioned gas source 914 is connected to the gas inlet 911 through a conduit 913, while the gas outlet 912 is connected through a conduit 915 to the above-mentioned ICP spectrometer 906. The laser irradiating port 907a of the cell 907 can be projected forward and retracted backward by the operation of a fluid cylinder (not shown) so as to be brought, when projected, into contact with the specimen 901.

The specimen cutting device 903 may incorporate a grinder disk 903b which is driven to rotate at a high speed by a motor 903a. The specimen chucking conveyor 904 includes a carriage 916 movable along rails laid between the laser analyzer 902 and the specimen cutting device 903 and a chuck 918 provided on the carriage 916 and adapted for chucking the specimen 901. The chuck 918 has a fixed first finger 919 and an opposing movable second finger 920 which is horizontally movable by the operation of, for example, a fluid cylinder (not shown) towards and away from the first finger 919. The second finger 920 is supported at its intermediate portion by a pin 921 for horizontal rotational movement.

The specimen 901 in red-heated state is prepared by picking, through a sub-lance, part of a steel melt up from a converter under operation and pouring the steel melt into a specimen mold. The red-heated specimen 901 thus prepared is held by the chuck 918 on the carriage 916 by the cooperation between the first and second fingers 919, 920. The carriage 916 is then driven towards the cutting device 903 to a position indicated by B in FIG. 27. Consequently, the red-heated specimen 901 is cut by the grinder 903a of the cutting device 903 rotating at a high speed, so that the analytical surface of the specimen to be examined is exposed. Only light load is imposed on the cutting device during the cutting because the specimen 901 is still hot when it is cut, so that the cutting can be finished in a short time.

Immediately after the analytical surface of the specimen is exposed as a result of the cutting of the specimen performed by the cutting device 903, the carriage 916 is moved towards the laser analyzer 902 to a position which is indicated by C in FIG. 27. Subsequently, the fluid pressure cylinder of the laser analyzer 902 is activated to project the cell 907 towards the Analytical surface of the specimen 901 chucked by the chuck 918 on the carriage 916, so as to bring the laser beam irradiating port 907a on the end of the cell into close contact with the analytical surface of the specimen 901. A high degree of closeness of contact can be obtained because the analytical surface of the specimen exposed as a result of the cutting is inherently smooth.

Then, the laser oscillator 905 is activated to emit laser beam. The laser beam thus emitted is reflected by a pair of reflective mirrors 909 arranged above and below the level of the laser oscillator 905, and is made to be incident to the condenser lens 910. The laser beam then enters the cell 907 through the quartz glass window 907a and is emitted through the irradiation port 907a so as to irradiate the analytical surface of the specimen 901. Meanwhile, argon gas is supplied into the cell 907 from the gas source 914, via the gas inlet 911. Fine particles which are released as a result of evaporation of the specimen material are introduced into the ICP analyzer 906 via the gas outlet 912 and through the conduit 915, and are excited to illuminate by the energy of a plasma so as to be analyzed by spectroscopy.

The plasma in the ICP spectrometer 906 is mainly composed of the plasma generated as a result of excitation of argon which can advantageously be excited with smaller energy as compared with nitrogen and oxygen. The plasma, therefore, is likely to be extinguished when air, i.e., oxygen and nitrogen, is introduced into the system, making it impossible to execute the spectroscopy. Introduction of air also causes oxidation of the specimen, changing carbon of the specimen material into, for example, carbon monoxide. Since the ICP spectrometer is unable to distinguish vapor phase and fine particles from each other, introduction of air constitute a serious error factor in the analysis and, hence, should be avoided as possible. In the described embodiment of the present invention, introduction of air is prevented almost perfectly, so that the analysis can be performed with high degrees of reliability and stability, by virtue of the tightness of the seal formed between the laser beam irradiating port 907a of the cell 907 and the specimen 901, thanks to the high degree of closeness of contact therebetween.

A description will now be given of the operation of the described apparatus of the present invention employed in the analysis of molten steel in a converter, by way of example. The operation was conducted by using a frusto-conical specimen of 70 mm tall, having diameters of 30 mm and 33 mm, respectively, at its bottom and top ends. The specimen was prepared by dipping into a steel melt in a converter a probe attached to an end of a sub-lance, and casting the steel melt into this probe.

The specimen 901 having a surface temperature of about 1000° C. and, hence, still red-heated was stationed at a position marked by A in FIG. 27 and was held by the chuck 918 on the carriage 916 of the specimen chuck conveyor 904 by being chucked between the first and second fingers 919, 920 of the chuck 918. Then, the carriage 916 was moved towards the specimen cutting device 903 to the position marked by B in FIG. 27 and the specimen 901 was cut by the grain disk 903b rotating at a high speed on the cutting device 903, whereby the analytical surface of the specimen 901 was exposed. Immediately after the cutting, the carriage 916 was moved towards the laser analyzer 902 so as to be stationed at the position indicated by C in FIG. 27. The timing and velocity of movement of the carriage 916 of the specimen chucking conveyor 904 were controlled by a controller which is not shown.

The analysis was conducted by using the laser analyzer of the following specifications:

Cell: A frusto-conical cell of 70 mm long, with the diameters of 10 mm and 50 mm, respectively, at the ends having the irradiation port 907a and the quartz glass window 907b.

Laser: An Nd-YAG laser (wavelength 1.06 $\mu$m) with a supersonic Q switch was used as the laser.

Carrier gas: argon gas was used as the carrier gas.

Analyzer: An ICP spectrometer was used as the analyzer.

The fluid pressure cylinder of the laser analyzer 902 was activated so that the cell 907 was projected towards the specimen 901 chucked by the chuck 918 on the carriage 916 and is then pressed onto the specimen 901 into close contact therewith. Then, the laser oscillator 905 was activated so that the specimen 901 was irradiated with a 1 KHz pulsating laser beam of an average power of 12 W.

The irradiating laser beam was condensed to form a beam spot of 100 $\mu$m or less on the specimen 901, through the condenser lens 910 which was designed to have a focal length of 75 mm. The focal position was controlled by changing the optical axis of the laser beam through varying the reflecting angles of the pair of reflective mirrors arranged above and below the optical axis between the condenser lens 910 and the laser oscillator 905. Each of the reflective mirrors was 20 mm wide and 30 mm long, and was held by a mechanism for varying the angle and period of beam oscillation. More specifically, one of the reflective mirrors was rotatable at a period or frequency of 30 Hz so as to oscillate the focal point at an amplitude of 2 mm, while the other was rotatable to oscillate the focal point at a frequency of 3 KHz over an amplitude of 2 mm.

A preparatory laser beam irradiation was effected on the surface of the specimen 901 for 25 seconds so as to get rid of layers which hamper the analysis, e.g., an oxide film and a contaminant film. Then, fine particles were released from the specimen material as a result of a subsequent irradiation with laser beam and were conveyed to the ICP analyzer 906 so as to be subjected to the analysis through spectroscopy. The duration of the preparatory irradiation with the laser beam may be shorter than 25 seconds, provided that the oxide and contaminant films are effectively removed. Leaving the cell 907 open for a long time undesirably allows invasion of the system by the ambient air, so that a laborious and time-consuming work is necessary for the purpose of substituting the invading air with the inert gas and removal of dews depositing to the inner surfaces of the cell and tubes, thus prolonging the time of preparation prior to the analysis. It is therefore necessary to keep the laser beam irradiation port 907a of the cell 907 closed during suspension of the analysis so as to minimize the time over which the cell is opened. It is also advisable, for the same reason, that the conduits 913, 914 have small diameters as possible. In the illustrated embodiment, tubes having diameters of 2 mm were used as the conduits 913, 914.

The fine particles released from the specimen 901 as a result of irradiation with the laser beam were conveyed, by means of the argon gas supplied into the cell 907 through the gas inlet 911, into the ICP spectrometer 906 via the gas outlet 912 and through the conduit 915. It is to be noted that any impurity in the argon gas, as well as the material of the conduit 915, adversely affects the accuracy of analysis of the specimen, in particular the accuracy of determination of C content. In the described example, therefore, the argon gas was purified by Zr-getter technique so as to reduce the C concentration in the gas down below 1 $\mu$g/r, and a stainless steel tube with a cleaned inner surface was used as the conduit 915, so as to maintain the content of C in the analyzing atmosphere at a level almost the same as that required in determination of C content in analysis of steels by ordinary techniques. The C concentration of commercially available purified argon gas generally ranges between 4 $\mu$g/liter and 5 $\mu$g/liter. It was confirmed that the C concentration can further be reduced to 0.2 $\mu$g/liter, through the above-mentioned Zr-getter type purifying process.

The ICP spectrometer was operated at a frequency of 27.12 MHz with a power of 1.5 KW, while maintaining the flow rates of the plasma gas, auxiliary gas and the carrier gas at 15 liter/min, 1 liter/min and 1 liter/min, respectively, so as to directly excite the fine particles released as a result of evaporation of the specimen material, thereby causing these fine particles to illuminate.

A Paschen-Runge spectrometer was used as the analyzer in this example. The spectrometer was evacuated to enable measurement even at wavelengths below 20 nm. The analysis was conducted by using, as analyzing rays, C:193 nm, P:178 nm, S:191 nm, Si:212 nm, Mn:252 nm, Al:396 nm, Ni:232 nm, Cr:268 nm, Mo:202 nm, Cu:325 nm, Fe:271 nm and 170 nm. The measurement was carried out by using a multi-element simultaneous measuring system in which a slit and a photoelectron multiplier tube were arranged in each of the analytical position.

The intensity of light was changed by the photoelectron multiplier tube into electrical current which was then converted into voltage. The voltage value was integrated over a period of 10 seconds, thus determining the measured light intensity. The analysis relied upon intensity comparison method in which each light intensity was determined in terms of ratio to the Fe intensity. For the purpose of converting the measured values into the analytical values, a standard specimen having a known composition was subjected to the same measurement to provide working curves, and the analytical values, i.e., the contents, of the elements were determined by conversion from the measured values based on the working curves.

The time required for the analysis inclusive of the time for picking up of the specimen from the probe was as short as 60 seconds, which is less than half that (140 seconds) required in conventional techniques. Thus, the analysis time is remarkably shortened by the present invention. It is also to be noted that the specimen can be stably set without being affected by burrs which are generated when the red-heated specimen is picked up from the probe, thanks to the cutting of the specimen 901 by the cutting device 3.

What is claimed is:

1. A method for analyzing a solid specimen comprising the steps of:

(a) preparing a pulsed laser beam having a frequency of at least 100 Hz and a half width of 1 μsec or less;

(b) determining a laser irradiation region so that an energy density satisfies the following equation:

$$Q > t^{1/2} \times \alpha/r$$

where

Q represents the energy density (J/cm$^2$);

t represents the pulse half width;

α represents a parameter inherent in the solid specimen; and r represents an absorption coefficient of the laser beam;

(c) irradiating the pulsed laser beam having said irradiation region on a surface of the solid specimen in an inert gas stream and vaporizing a part of the solid specimen to generate fine particles;

(d) repeating the step (c) on the same surface that the pulsed laser beam is irradiated at the step (c) to generate further fine particles;

(e) transferring said fine particles formed in steps (c) and (d) to a detector; and (f) performing elemental analysis in the detector.

2. A method according to claim 1, wherein the step (c) of irradiating the pulsed laser beam comprises irradiating the pulsed laser beam from a laser oscillating means including a semiconductor laser.

3. A method according to claim 2, wherein said laser oscillating means comprises:

a semiconductor laser for emitting the laser beam;

a laser rod for receiving the laser beam from said semiconductor laser and oscillating a single mode laser beam by optical amplification; and an optical transfer cable for connecting said semiconductor laser with said laser rod.

4. A method according to claim 2, wherein said laser oscillating means comprises:

a semiconductor laser for emitting a laser beam as pumping light;

a laser rod for receiving and optically amplifying said laser beam from said semiconductor laser; and resonators arranged at the both sides of said laser rod.

5. A method according to claim 4, wherein said laser oscillating means further comprises an optical transfer cable for connecting said semiconductor laser with said laser rod.

6. A method according to claim 1, wherein the step (c) of irradiating the pulsed laser beam comprises irradiating the pulsed laser beam by scanning two-dimensionally so that the irradiation regions are overlapped each other.

7. A method according to claim 1, wherein said laser irradiation region has a diameter of 10 to 500 μm.

8. A method according to claim 1, wherein the step (d) of repeating the step (c) is carried out at least two times.

9. A method for analyzing a solid specimen including an element in the form of a solid solution and the element in the form of a compound, comprising the steps of:

continuously moving a position of a solid specimen to be analyzed at a predetermined speed;

irradiating a pulsed laser beam on the solid specimen to generate fine particles;

repeatedly measuring a composition of the fine particles at a minute time interval to obtain a plurality of momentary values, the momentary values being of a waveform having peaks and troughs;

determining an amount of the element existing in the form of the solid solution based on the momentary values of the troughs; and determining an amount of the element existing in the form of the compound based on the momentary values.

* * * * *